US006710169B2

(12) United States Patent
Capon et al.

(10) Patent No.: US 6,710,169 B2
(45) Date of Patent: *Mar. 23, 2004

(54) ADHESON VARIANTS

(75) Inventors: Daniel J. Capon, San Mateo, CA (US); Timothy J. Gregory, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/157,408

(22) Filed: May 28, 2002

(65) Prior Publication Data

US 2003/0104535 A1 Jun. 5, 2003

Related U.S. Application Data

(63) Continuation of application No. 09/641,554, filed on Aug. 17, 2000, now abandoned, which is a continuation of application No. 09/275,310, filed on Mar. 24, 1999, now abandoned, which is a continuation of application No. 08/457,918, filed on Jun. 1, 1995, now Pat. No. 6,117,655, which is a continuation of application No. 08/236,311, filed on May 2, 1994, now Pat. No. 5,565,335, which is a continuation of application No. 07/936,190, filed on Aug. 26, 1992, now Pat. No. 5,336,603, which is a division of application No. 07/842,777, filed on Feb. 18, 1992, now abandoned, which is a continuation of application No. 07/250,785, filed on Sep. 28, 1988, now abandoned, which is a continuation-in-part of application No. 07/104,329, filed on Oct. 2, 1987, now abandoned.

(51) Int. Cl.$^7$ ...................... C07K 14/705; C07K 14/73; C12N 15/62
(52) U.S. Cl. ................... 530/387.3; 530/350; 536/23.4; 435/69.7
(58) Field of Search ........................... 530/387.1, 387.3, 530/350; 536/23.4; 435/69.7

(56) References Cited

U.S. PATENT DOCUMENTS

| 3,959,080 A | 5/1976 | Orth et al. |
| 4,002,531 A | 1/1977 | Royer |
| 4,055,635 A | 10/1977 | Green et al. |
| 4,301,144 A | 11/1981 | Iwashita et al. |
| 4,412,989 A | 11/1983 | Iwashita et al. |
| 4,444,878 A | 4/1984 | Paulus et al. |
| 4,745,055 A | 5/1988 | Schenk |
| 4,761,371 A | 8/1988 | Bell et al. |
| 4,766,106 A | 8/1988 | Katre et al. |
| 4,816,567 A | 3/1989 | Cabilly et al. |
| 4,879,211 A | 11/1989 | Wang et al. |
| 5,336,603 A | 8/1994 | Capon et al. |

FOREIGN PATENT DOCUMENTS

| EP | 068763 | 1/1983 |
| EP | 088695 | 9/1983 |
| EP | 120694 | 10/1984 |
| EP | 139416 | 5/1985 |
| EP | 173494 | 3/1986 |
| EP | 244221 | 11/1987 |
| EP | 255694 | 2/1988 |
| EP | 256654 | 2/1988 |
| EP | 266663 | 5/1988 |
| EP | 278776 | 8/1988 |
| EP | 296786 | 12/1988 |
| EP | 313377 | 4/1989 |
| EP | 319815 | 6/1989 |
| EP | 325262 | 7/1989 |
| EP | 330227 | 8/1989 |
| EP | 331356 | 9/1989 |
| WO | WO 85/03947 | 9/1985 |
| WO | WO 87/03600 | 6/1987 |
| WO | WO 88/01304 | 2/1988 |
| WO | WO 88/03559 | 5/1988 |
| WO | WO 88/07376 | 10/1988 |
| WO | WO 88/09344 | 12/1988 |
| WO | WO 89/01940 | 3/1989 |
| WO | WO 89/03221 | 4/1989 |

OTHER PUBLICATIONS

Allaway et al., "Expression and Characterization of CD4–IgG$_2$, a Novel Heterotetramer That Neutralizes Primary HIV Type 1 Isolates" *Aids Research and Retroviruses* 11 (5):533–539 (1995).

Amster et al., "Synthesis of part of a mouse immunoglobulin light chain in a bacterial clone" *Nucl. Acids Res.* 8(10):2055–2065 (1980).

Anderson et al., "Regulatory Interactions Between Members of the Immunoglobulin Superfamily" *Immunology Today* 9 (7 & 8):199–203 (1988).

Aruffo et al., "CD44 is the Principal Cell Surface Receptor for Hyaluronate" *Cell* 61:1303–1313 (1990).

Beauchamp et al., "A new procedure for the synthesis of polyethylene glycol–protein adducts; effects on function, receptor recognition, and clearance of superoxide dismutase, lactoferrin, and $\alpha_2$–macroglobulin" *Analytical Biochemistry* 131(1):25–33 (1983).

Blank et al., "Complete structure and expression in transfected cells of high affinity IgE receptor" *Nature* 337(6203):187–189 (1989).

Boulianne et al., "Production of functional chimaeric mouse/human antibody" *Nature* 312:643–646 (Dec. 13, 1984).

Byrn et al., "Biological Properties of a CD4 Immunoadhesin" *Nature* 344:667–670 (Apr. 12, 1990).

(List continued on next page.)

Primary Examiner—Prema Mertz
(74) Attorney, Agent, or Firm—Jeffrey S. Kubinec

(57) ABSTRACT

Novel derivatives of cell surface proteins which are homologous to the immunoglobulin superfamily (adhesons) are provided. Amino acid sequence variations are introduced into adheson, the most noteworthy of which are those in which the transmembrane and, preferably, cytoplasmic domains are rendered functionally inactive, and in which adheson extracellular domains replace an immunoglobulin variable region. These variants are useful in therapy or diagnostics, in particular, CD4 variants are therapeutically useful in the treatment of HIV infections.

19 Claims, 13 Drawing Sheets

OTHER PUBLICATIONS

Capon et al., "Designing CD4 Immunoadhesins for AIDS Therapy" *Nature* 337:525–531 (1989).

Chamow et al., "A Humanized Bispecific Immunoadhesin–Antibody That Retargets CD3+ Effectors to Kill HIV–1–Infected Cells" *Journal of Immunology* 153:4268–4280 (1994).

Chaudhary et al., "Activity of a recombinant fusion protein between transforming growth factor type alpha and Pseudomonas toxin" *Proc. Natl. Acad. Sci. USA* 84:4538–4542 (1987).

Clark et al., "Peptide and nucleotide sequences for rat CD4 (W3/25) antigen: Evidence for derivation from a structure with four immunoglobulin–related domains" *Proc. Natl. Acad. Sci.* 84:1649–1653 (1987).

Clerici et al., "Effect of a Recombinant CD4–IgG on In Vitro T Helper Cell Function: Data From a Phase I/II Study of Patients with AIDS" *The Journal of Infectious Diseases* 168:1012–1016 (1993).

Estess et al., "Analysis of T–cell receptor structure and function using chimeric T–cell receptor/immunoglobulin molecules" *Journal of Cellular Biochemistry Supplement* 11 (Part D, Abs. 331) :258 (1987).

Falkner and Zachau, "Expression of mouse immunoglobulin genes in monkey cells" *Nature* 298:286–288 (1982).

Gascoigne et al., "Secretion of a Chimeric T–cell Receptor–immunoglobulin Protein" *Proc. Natl. Acad. Sci. USA* 84:2936–2940 (1987).

Gascoigne et al., "Secretion of chimeric T cell receptor–immunoglobulin fusion proteins" *Journal of Cellular Biochemistry Supplement* 11 (Part D, Abs. 333):259 (1987).

Goverman et al., "Chimeric T–cell receptor genes as tools in analyzing T–cell/target–cell interactions" *Journal of Cellular Biochemistry Supplement* 11 (Part D, Abs. 334) :259 (1987).

Haak–Frendscho et al., "Human IgE Receptor α chain–IgG Chimera Blocks Passive Cutaneous Anaphylaxis Reaction In Vivo" *J. Immunol.* 151(1) :351–358 (1993).

Hakimi et al., "The α subunit of the human IgE receptor (FcERI) is sufficient for high affinity IgE binding" *Journal of Biological Chemistry* 265(36):22079–22081 (1990).

Hashimoto et al., "Rearrangement and expression of T cell receptor genes in pre–T cells" *Journal of Cellular Biochemistry Supplement* 11 (Part D, Abs. 434):278 (1987).

"Human Immunodeficiency Virus Infection" *The Merck Manual of Diagnosis and Therapy*, Mark H. Beers and Robert Berkow, M.D., 17th edition, Whitehouse Station, N.J.:Merck Research Laboratories, Chapter 163, pp. 1312–1323 (1999).

Ivars et al., "Expression of cloned T cell receptor genes" *Journal of Cellular Biochemistry Supplement* 11 (Part D, Abs. 435) :278 (1987).

Johnson et al., "Correlation of T cell receptor structure and function" *Journal of Cellular Biochemistry Supplement* 11 (Part D, Abs. 337):260 (1987).

Kahn et al., "A Phase 1 Study of Recombinant Human CD4 Immunoglobulin G (rCD4–IgG) In Patients With HIV–Associated Immune Thrombocytopenic Purpura", (W.B. 2156) pp. 221 (1991).

Kohler, G., "Immunoglobulin chain loss in hybridoma lines" *Proc. Natl. Acad. Sci. USA* 77(4):2197–2199 (1980).

Linsley et al., "Binding of the B Cell Activation Antigen B7 to CD28 Costimulates T Cell Proliferation and Interleukin 2 mRNA Accumulation" *Journal of Experimental Medicine* 173:721–730 (1991).

Linsley et al., "CTLA–4 is a second receptor for the B cell activation antigen B7" *Journal of Experimental Medicine* 174:561–569 (1991).

Littman DR, "The isolation and sequence of the gene encoding T8: a molecule defining functional classes of T lymphocytes" *Cell* 40(2):237–246 (1985).

Littman DR, "The structure of the CD4 and CD8 genes" *Annual Review of Immunology* 5:561–584 (1987).

Maddon et al., "The isolation and Nucleotide Sequence of a cDNA Encoding the T Cell Surface Protein T4: A New Member of the Immunoglobulin Gene Family" *Cell* 42:93–104 (1985).

Maddon et al., "The T4 Gene Encodes the AIDS Virus Receptor and Is Expressed in the Immune System and the Brain" *Cell* 47:333–348 (1986).

Maddon P. et al., "Structure and expression of the human and mouse T4 genes" *Proc. Natl. Acad. Sci. USA* 84 (24):9155–9159 (1987).

McDougal et al., "Binding of HTLV–III/LAV to T4+ Cells by a Complex of the 110k Viral Protein and the T4 Molecule" *Science* 231:382–385 (1986).

McDougal et al., "The T4 Glycoprotein Is a Cell–Surface Receptor for the AIDS Virus" *Molecular Biology of Homosapiens* (Cold Spring Harbor Symposia on Quantitative Biology), New York:CSHL vol. LI (1986).

Miller, Larry et al., "Expression of high–affinity binding of human immunoglobulin E by transfected cells" *Science* 244:334–336 (1989).

Morrison et al., "Chimeric Human Antibody Molecules: Mouse Antigen–Binding Domains with Human Constant Region Domains" *Proc. Natl. Acad. Sci. USA* 81:6851–6855 (Nov. 1984).

Morrison et al., "Genetically Engineered Antibody Molecules and Their Application" *Biological Approaches to the Controlled Delivery of Drugs*, Annals of the New York Academy of Sciences, New York, New York:The New York Academy of Sciences vol. 507:187–198 (1987).

Morrison et al., "Transfer and expression of immunoglobulin genes" *Annual Review of Immunology* 2:239–256 (1984).

Morrison, J., "Sequentially derived mutants of the constant region of the heavy chain of murine immunoglobulins" *J. of Immunology* 123(2):793–800 (1979).

Morrison, S. L., "Transfectomas Provide Novel Chimeric Antibodies" *Science* 229:1202–1207 (Sep. 20, 1985).

Murre et al., "Biochemical and functional analyses of a secreted H–2L$^d$ molecule" *Molecular & Cellular Biology* 6:1315–1319 (1986).

Neuberger et al., "Recombinant Antibodies Possessing Novel Effector Functions" *Nature* 312:604–608 (Dec. 13, 1984).

Oi et al., "Chimeric Antibodies" *BioTechniques* 4(3) :214–221 (1986).

Osborn, L. et al., "Direct expression cloning of vascular cell adhesion molecule 1, a cytokine–induced endothelial protein that binds to lymphocytes" *Cell* 59:1203–1211 (1989).

Peterson, A.S., "Genetic analysis of CD2/LFA–3 and CD4/HIV interactions" (thesis), Harvard University, Chapter 1, (1988).

Putney et al., "HTLV–III/LAV neutralizing antibodies to an *E.coli*" *Science* 234:1392–1395 (1986).

Rose and Bergmann, "Expression from Cloned cDNA of Cell–Surface Secreted Forms of the Glycoprotein of Vesicular Stomatitis Virus in Eucaryotic Cells" *Cell* 30:753–762 (1982).

Rosenblum et al., "Modification of human leukocyte interferon pharmacology with a monoclonal antibody" *Cancer Research* 45:2421–2424 (1985).

Salzawa et al., "The CD4 molecule is associated with the T–cell receptor" *Journal of Cellular Biochemistry Supplement* 11 (Part D, Abs. 421):273 (1987).

Schacker et al., "The Effects of High–Dose Recombinant Soluble CD4 on Human Immunodeficiency Virus Type 1 Viremia" *The Journal of Infectious Diseases* 169:37–40 (1994).

Seed B., "An LFA–3 cDNA encodes a phospholipid–linked membrane protein homologous to its receptor CD2" *Nature* 329:840–842 (1987).

Sharon et al., "Expression of a $V_H C_\kappa$ chimaeric protein in mouse myeloma cells" *Nature* 309:364–367 (1984).

Shearer et al., "Transport of Recombinant Human CD4–Immunoglobulin G Across the Human Placenta: Pharmacokinetics and Safety in Six Mother–Infant Pairs in AIDS Clinical Trial Group Protocol 146" *Clinical and Diagnostics Laboratory Immunology* pp. 281–285 (1995).

Sleckman et al., "Expression and function of CD4 in a murine T–cell hybridoma" *Nature* 328 (6128):351–353 (1987).

Smith et al., "Blocking of HIV–1 Infectivity by a Soluble, Secreted Form of the CD4 Antigen" *Science* 238:1704–1707 (1987).

Springer and Strominger, "Detergent–soluble HLA antigens contain a hydrophilic region at the COOH–terminus and a penultimate hydrophobic region" *Proc. Natl. Acad. Sci. USA* 73(7):2481–2485 (1976).

Stamenkovic et al., "The B Lymphocyte Adhesion Molecule CD22 Interacts with Leukocyte Common Antigen CD45RO on T Cells and α2–6 Sialyltransferase, CD75, on B Cells" *Cell* 66:1133–1144 (1991).

Terhorst C. et al., "Biochemical analysis of human T lymphocyte differentiation antigens T4 and T5" *Science* 209(4455):520–521 (1980).

Traunecker et al., "A novel approach for preparing anti–T cell receptor constant region antibodies" *European Journal of Immunology* 16:851–854 (1986).

Traunecker et al., "Highly Efficient Neutralization of HIV with Recombinant CD4–immunoglobulin Molecules" *Nature* 339:68–70 (1989).

Traunecker et al., "Soluble CD4 molecules neutralize human immunodeficiency virus" *Nature* 331:84–86 (1988).

Ushijima et al., "Synergistic Effect of Recombinant CD4–Immunoglobulin in Combination with Azidothymidine, Dideoxyinosine and 0.5 β–monoclonal Antibody on Human Immunodeficiency Virus Infection in vitro" *Letters in Applied Microbiology* 19:1–5 (1994).

Vitetta et al., "Redesigning Nature's Poisons to Create Anti–Tumor Reagents" *Science* 238:1098–1104 (1987).

Ward et al., "Prevention of HIV–1 IIIB Infection in Chimpanzees by CD4 Immunoadhesin" *Nature* 352:434–436 (1991).

Wills et al., "Mutations of the Rous Sarcoma Virus env Gene that affect the transport and subcellular location of the glycoprotein products" *Journal of Cell Biology* 99:2011–2023 (1984).

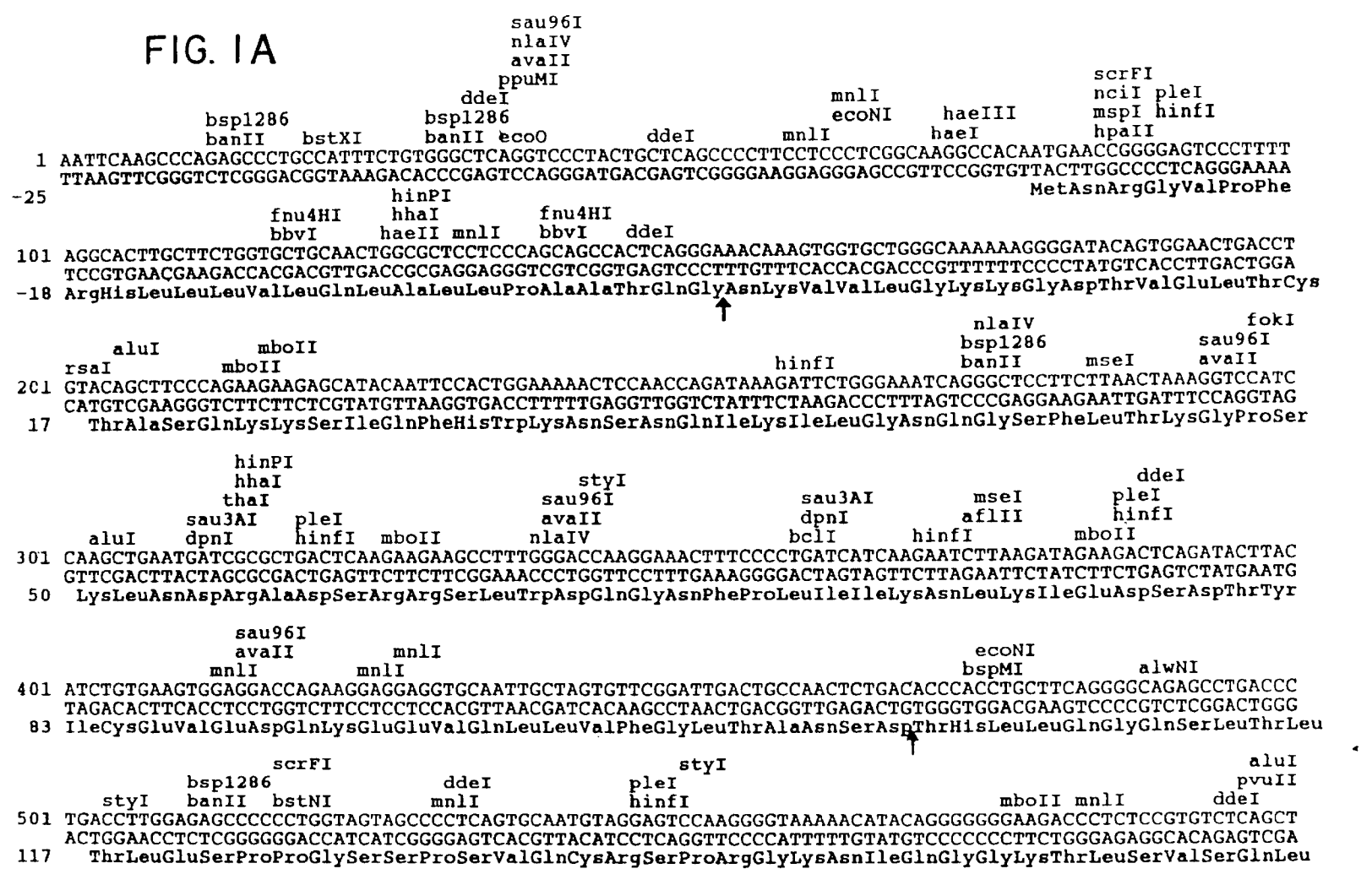

```
                    bstXI
         aluI
         sacI bstNI              scrFI
         hgiAI                   bstNI                                                                                  mnlI
         bsp1286       nlaIV                                                   aluI                                     haeIII
         banII  banI              nlaIII             mboII                     nheI                              aluI   stuI
                                                                                                                        haeI
601  GGAGCTCCAGGATAGTGGCACCTGGCACATGTCTCTTGCAGAACCAGAAGAAGGTGGAGTTCAAAATAGACATCGTGTCTGCTAGCTTTCCAGAAGCC
     CCTCGAGGTCCTATCACCGTGGACCGTGTACAGAGAACGTCTTGGTCTTCTTCCACCTCAAGTTTTATCTGTAGCACAGACGATCGAAAGGTCTTCGG
150  GluLeuGlnAspSerGlyThrTrpThrCysSerThrValLeuGlnAsnGlnLysLysValGlnPheLysIleAspIleValAlaPheGlnLysAla
                                                 mnlI                          aluI                        aluI
701  TCCAGCATAGTCTATAAGAAGAGGGGAACAGGTGGAGTTCTCCTTCCCACTCGCTTTACAGTTGAAAAGCTGACGGGCAGTGGCGAGCTGTGGTGGC
     AGGTCGTATCAGATATTCTTCTCCCCTTGTCCACCTCAAGAGGAAGGGTGAGCGAAATGTCAACTTTTCGACTGCCCGTCACCGCTCGACACCACCG
183  SerSerIleValTyrLysLysGluGlyAsnArgTrpSerSerSerProLeuValLeuGlnLeuPheSerPheAlaLeuGlnValGluLysLeuThrGlySerGlyGluLeuTrpTrpGln
                                                                                             sau96I
                                                                                             nlaIV
                                                                                             avaII
                                          hphI                                               ppuMI
                                          sau3AI                                             scrFI
                    mnlI          pflMI   dpnI                                               bstNI                  aluI
             mnlI   mnlI   mnlI   alwI    alwI                              mboII            bstEII  ecoO    ddeI
801  AGGCGGAGAGGGCTTCCTCCTCCAAGTCTTCCAAGTCTTGGATCACCTTTGACCTGAAGAACAAGGAAGTGTCTGTAAAACGGTTACCCAGACCCTAAGCTCCAGAT
     TCCGCCTCTCCCGAAGGAGGAGGTTCAGAACCTAGTGGAACTGGACTTCTGTCCTTCACAGACATTTTGCCAATGGGTCTGGATTCGAGGTCTA
217  AlaGluArgAlaSerSerSerLysSerTrpIleThrPheAspLeuLysAsnLysGluValSerValLysArgValThrGlnAspProLysLeuGlnMet
```

```
                                                             sau96I
                haeIII                                       scrFI
                stuI                                         hphI haeIII
                haeI        ddeI                             mnlI bstNI
         hphI   scrFI       mnlI
     aluI   mnlI econI bstNI
901  GGGCAAGAAGCTCCCGCTCCACCTGAGCTCTGCCTCTGCCTCCTCAGTATGCTGGCTCTGGAAACCTCACCTGGCCCTTGAAGCGAAAACAGGAAAG
     CCCGTTCTTCGAGGGCGAGGTGGACGGGTCCGAACGGAGTCATACGACCGAGACCGAGACCTTGGAGTGGACCGGGAACTTCGCTTTTGTCCTTTC
250   GlyLysLysLeuProLeuHisLeuProGlnAlaLeuProGlnAlaLeuProGlnTyrAlaGlySerGlyAsnLeuThrLeuAlaLeuAlaLysThrGlyLys sau96I
                                                              nlaIV
                                                              avaII
                                                              ppuMI
              scrFI              aluI                         nlaIV           aluI   ddeI
              bstNI hphI         ddeI              mnlI       ecoO  mnlI ddeI  sfaNI
     sfaNI
1001 TTGCATCAGGAAGTGAACCTGGTGGTGATGAGACCCACTCAGCTCCAGAAAAATTTGACCTGTGAGGTGTGGGACCCACCTCCCCTAAGCTGATGCTGA
     AACGTAGTCCTTCACTTGGACCACCACTACTCTGGGTGAGTCGAGGTCTTTTTAAACTGGACACTCCACACCCTGGGTGGAGGGGATTCGACTACGACT
283   LeuHisGlnGluValAsnLeuValValMetArgAlaThrGlnLeuGlnLysAsnLeuThrCysGlnValThrGlyProThrSerProLysLeuMetLeuSer pleI
              mnlI                                            alwNI  ddeI hinfI
              ddeI                 taqI              fokI
              mstII
             eco81I
1101 GTTTGAAACTGAGAACAAGGAGCAAAGGTCTCGAAGCGGGAGAAGCCGTGGGTGCTGAACCCTGAGGCGGGGATGGCAGTGTCTGCTGAGTGA
     CAAACTTTGACTCTTGTTCCTCGTTTCCAGAGCTTCCGCCCTCTTCGGCACCCACTTGGGACTCCGCCCTACACCGTCACAGACGACTCACT
317   LeuLysLeuGluAsnLysGluAlaLysValSerLysArgGluLysArgGluLysAlaValValTrpValLeuAsnProAlaAlaGlyMetAlaValSerLeuLeuSerAsp
```

FIG. 1B-2

```
        sau96I
        avaII
        ppuMI                                                              sau96I
        ecoO            hinfI                          nlaIII  avaII   alul   mseI
     avaI  alwNI                                                  avaI        alul    mseI
1201 CTCGGGACAGGTCCTGCTGGAATCTGAACATCAAGGTTCTGCCCACATGGTCCACCCCGAGCTTTAATGCGGTAGTTTATCACAGTTAAATTGCTAACGCA
     GAGCCCTGTCCAGGACGACCTTAGTTGTAGTTCCAAGACGGGTGTACCAGGTGGGGCTCGAAATTACGCCATCAAATAGTGTCAATTTAACGATTGCGT
 350 SerGlyGlnValLeuLeuGluSerAsnIleLysValLeuProThrTrpSerPheProSerPheAsnAlaValValTyrHisSerOC* sfaNI                      scrFI
                                                                scrFI                      nciI
                   hinPI           mnlI       nlaIV          bstNI                    rsaI mspI
            nlaIV  hhaI     fokI   fokI  banI hphI  fokI                         mspI hpaII hpaII
1301 GTCAGGCACCGTGTATGAAATCTAACAATGCGCTCATCGTCATCCTCGGCACCGTCACCCTGATGCTGAGCCTGTAGGCATAGGCTTGGTTATGCCGGTACTGCC
     CAGTCCGTGGCACATACTTTAGATTGTTACGCGAGTAGCAGTAGGAGCCGTGGCAGTGGGACTACGACTCGGACATCCGTATCCGAACCAATACGGCCATGACGG
         mnlI
         haeIII
         sau96I
1401 GGGCCTCTTGCGGGAT
     CCCGGAGAACGCCCTA
```

```
                                                                                          scrFI
                                                                                          bstXI
                                                                                           aluI
                                                                                      sacI bstNI
                                                                                      aluI hgiAI
                                                                                      pvuII bsp1286
                                                                                       ddeI banII
                    scrFI            styI                                  mboII mnlI
             bsp1286    ddeI   pleI                                                    mnlI
             banII bstNI  mnlI hinfI                                                   haeIII
                                                                                  aluI stuI
                                                                              nheI    haeI
     GAGAGCCCCCTGGTAGTAGCCAGTGCAATGTAGGAGTCCAAGGGTAAAACATACAGGGGGGAAGACCCTCCGTGTCTCAGCTGGAGCTCC
601  CTCTCGGGGGACCATCATCGGTCACGTTACATCCTCAGGTTCCCCATTTTGTATGTCCCCCCCTTCTGGAGAGGCACAGAGTCGACCTCGAGG
176  GluSerProSerProGlySerSerProSerValGlnCysArgSerProArgGlyLysAsnIleGlnGlyGlyLysThrLeuSerValSerGlnLeuGluLeuGln
                scrFI                                                              mnlI
                bstNI                                                        aluI
             banI   nlaIII                                                   nheI
           nlaIV         mboII
     AGGATAGTGGCACCTGGACATGCACTGTCTCTTGCAGAACCAGAAGAGTGGAGTTCAAAATAGACATCGTGGTGCTAGCTTTCCAGAAGGCCTCCAGCAT
701  TCCTATCACCGTGGACCTGTACGTGACAGAGAACGTCTTGGTCTTCTCACCTCAAGTTTTATCTGTAGCACCACGATCGAAAGGTCTTCCGGAGGTCGTA
210  AspSerGlyThrTrpThrCysThrValLeuGlnAsnGlnLysValGluPheLysIleAspIlePheLysValValLeuAlaPheGlnLysAlaSerSerIle
                                                                                                   mnlI
                mnlI                                        aluI     aluI
     AGTCTATAAGAAAGAGGGGGAACAGGTGGAGTTCTCCTTCCCACTCTGGAGTTGAAAAGCTGACGGGCCAGTGGGCGAGCTGTGGTGCAGGCGAG
801  TCAGATATTCTTTCTCCCCCTTGTCCACCTCAAGAGGAAGGGTGAGACGGTCAACTTTTCGACTGCCCGGTCGACACCACGTCCGCCTC
243  ValTyrLysGluGlyGluGlnValGluPheSerPheProLeuAlaPheThrValGluLysLeuThrGlySerGlyLeuThrGlyLeuTrpTrpGlnAlaGlu
                                                                     sau96I
                                                                     nlaIV
                                                                      avaII
                                                                     ppuMI
                                                                      scrFI
                hphI                                                 bstNI
                sau3AI                                          bstEII ecoO ddeI     aluI
                dpnI
        mnlI pflMI   alwI                         mboII
     AGGGCTTCCTCCTCCAAGTCTTGGATCACCTTTGACCTGAAGAACAAGGAAGTGTCTGTAAAACGGGGTTACCAGGACCCTAAGCTCCAGATGGCAAGA
901  TCCCGAAGGAGGAGGTTCAGAACCTAGTGGAAACTGGACTTCTTGTTCCTTCACAGACATTTGCCCAATGGTCCTGGGATTCGAGGTCTACCCGTTCT
276  ArgAlaSerSerLysSerTrpIleThrPheAspLeuLysLysAsnLysGluValSerValLysArgValThrGlnAspProLysLeuGlnMetGlyLysLys
```

```
                                                           haeIII
                                                           stuI
                                                           haeI                        sau96I
                         hphI       scrFI      ddeI                                    scrFI
              mnlI       ecoNI    bstNI       mnlI                              hphI   haeIII                                sfaNI
      aluI                                                                      mnlI   bstNI
1001  AGCTCCCGCTCCACCTCCAAACCTCCACCCTGCCCCAGGCCCTGCCTCTGGCTCCAGTATGCTGCTCTGGAAACACCAGGAAAGCGAAAACAGGAAAGTTGCATCA
      TCGAGGGCGAGGTGGAGGTTTGGAGGTGGGACGGGGTCCGGGACGGAGGTCATACGACGAGACCGAGTCATACGACGAGACCCTTGAGTGGACTGGAGTGGACCGGAACTTCGCTTCTTGTCCTTTCAACGTAGT
310   LeuProLeuHisLeuThrLeuProGlnAlaLeuProGlnTyrAlaGlySerGlyAsnLeuThrLeuAlaLeuGluAlaLysThrGlyLysLeuHisGln sau96I
                                                                     nlaIV
                                                                     avaII
                                                                     ppuMI
                                                                     nlaIV         aluI
                              scrFI                                  ecoO   mnlI   ddeI   sfaNI
                   scrFI      hphI                           mnlI                         ddeI
              bstNI                          aluI
1101  GGAAGTGAACCTGGTGGTGATGAGAGCCACTCAGCTCGTGAGGTGTGGGGACCTCCCCTAAGCTGATGCTGAGTTTGAAA
      CCTTCACTTGGACCACCACTACTCTCGGTGAGTCGAGCTCTTTTAAACTGGACACTCCACACCCTGGGTGGAGGGGATTCGACTACGACTCAAACTTT
343   GluValAsnLeuValValMetArgAlaThrGlnLeuGlnLysAsnLeuThrCysGluValTrpGlyProThrSerProLysLeuMetLeuSerLeuLys
```

FIG. 2B-2

```
                                                              mnlI
                                                              ddeI            avaI
                                                              mstII           pleI
                                                    sfanI     eco81I   fokI   alwNI   ddeI  hinfI   alwNI
1201 CTGGAGAACAAGGAGGCAAAGGTCTCGAAGCGGGAGAAGGCGGTGTGGTGCTGAACCCTGAGGCGGGATGTGGCAGTGTCTGCTGAGTGACTCGGAC
     GACCCTCTTGTTCCTCCGTTTCCAGAGCTTCGCCCTCTTCCGCCACACCACGACTTGGGACTCCGCCCCTACACCGTCACAGACGACTCACTGAGCCTG
              mnlI       taqI
 376 LeuGluAsnLysGluAlaLysValSerLysArgGluLysValAlaValValLeuAsnProGluAlaGlyMetTrpGlnCysLeuLeuSerAspSerGlyGln sau96I                                     sau96I
         avaII                                      avaII                                           nlaIV
         ppuMI           hinfI           nlaIII     avaI    aluI            mseI                    banI
         ecoO                                                                                       
1301 AGTGCCTGCTGGAATCAACATCAAGTTCTGCCCACATGTCCCCCGAGCTTTAATGCGGTAGTTTATCACAGTTAATTGCTAACGCAGTCAGGCA
     TCCAGGACGACCTTAGTTGTAGTTCAAGACGGGTGTACCAGGGGGCTCGAAATTACGCCATCAAATAGTGTCAATTAACGATTGCGTCAGTCCGT
 410 ValLeuLeuGluLeuSerAsnIleLysValLeuProThrTrpSerThrProSerPheAsnAlaValValTyrHisSerOC* haeIII
                                                                                       sau96I
                                                                                       scrFI
                                                            sfaNI                rsaI  ncII
                                                            scrFI                mspI  mspI mnlI
                              hinPI        nlaIV            bstNI                hpaII hpaII
                              hhaI   fokI  mnlI  banI hphI  fokI
1401 CCGTGTATGAAATCTAACAATGCGCTCATCGTCATCCTCTCGGCACCGTCACCCTGGATGCTGTAGGCATAGGCTTGGTTATGCCGGTACTGCCGGGCCTCT
     GGCACATACTTTAGATGTTACGCGAGTAGCAGTAGGAGAGCCGTGGCAGTGGGACCTACGACATCCGTATCCGAACCAATACGGCCATGACGGCCCGGAGA

1501 TGCGGGAT
     ACGCCCTA
```

Immunoglobulin γ₁

Soluble rCD4

```
                                                                                           sau96I
                                                                                  taqI     nlaIV
                                                                                  sau3AI   ecoO
                                                                  rsaI     hgaI   dpnI     scrFI
                                                                                  alwI     bstNI
  1 GAATTCTGTCACTGCCGCGGACACGGCCGGCGCCTGTATATTACTGTGCGAGAGCCACCTTTGCCTATGTGACAGGAGCGTCCCCCTTGTTGATCGACCCTGG
    CTTAAGACAGTGACGGCGCCTGTGCCGGCCGCGGACATATAATGACACGCTCGGTGAAAACGATACCATGTCCCTCGCAGGGAACAACCTAGCTGGGACC
 72     ValThrAlaAlaAspThrAlaAlaValTyrTyrCysAlaaArgAlaThrPheCysLeuTrpTyrArgGluArgProProCysTrpIleAspProTrp
                         thaI      haeIII                                          sau96I
                         sacII     xmaII                                           sau96I
                         fnu4HI    eaeI                                            nlaIV
                                                                                   bsp1286
       nlaIV     hphI                                                              banII
       scrFI    bstEII                                          scrFI    mnlI      apaI
       bstNI     scrFI                                          bstNI    mnlI      ecoO                    sau96I
       haeIII    bstNI                 haeIII                            mnlI      hgiAI        mnlI       fnu4HI
 101 GGCCTGGGACCTGTCACCCTGGTCACCCTCGGCTCTCCACCAAGGGCCCATCCGTCTTCCCCTGGCACCCTCCTCCAAGAGCACCTCTCGGGGCACAGCGG
     CCGGACCCTTGGACAGTGGGACCAGTGGGAGCCGAGAGGTGGTTCCCGGGTAGCCAGAGGGGACCGTGGGAGGAGTTCTCGTGAGACCCCGTGTCGCC
 103    GlyLeuGlyThrLeuValThrLeuGlyProValPheProValPheLysThrLysProSerAlaSerThrSerGlyGlyThrAlaAla
                                                 hinPI
                                                 nlaIV
                                                 narI
                                                 haeII         hgiAI     mspI
                                                 banI          bsp1286   hpaII
                scrFI                      nlaIV ahaII                   scrFI
           fnu4HI  econI                   haeIII hhaI          fnu4HI   ncII
           bbvI    bstNI                   ddeI                          apaLI
 201 CCCTGGCGCTGCTCAAGGACTACTTCCCGAACCGTGACGGTGCTCGTGACACCGGTCCAGGCGCCCTGACCAGCGGCGTGCACACCTTCCCGGCTGTCCT
     GGGACCGCGACGAGTTCCTGATGAAGGGCTTGGCACTGCCACAGCACTGCCAGGCGCCCGGGACTGGTCGCCGCACGTGTGGAAGGGCCGACAGGA
 137    LeuGlyCysSerLysValLeuValLysAspTyrPheProGluProValThrValSerTrpAsnSerGlyAlaLeuThrSerGlyValHisThrPheProAlaValLeu
                                       bstXI   alwNI
             ddeI                      bstEII  nlaIV
             mstII  pleI      ddeI     mnlI    banI
             mnlI  hinfI      fnu4HI   bbvI    bsp1286                       hinfI
             eco81I   hphI    bstEII   bbvI    bsp1286
 301 ACAGTCCTGGCAGACTCTACTCCCTGACCAGCGGTGGTGACGGTCCCTCCAAGAGCTTGGGCACCCAGACCTACATCTGCAACGTGAATCACAAGCCCAGC
     TGTCAGGACCGTCTGAGATGAGGGACTGGTCGCCACCACTGCCAGGGAGGTTCTCGAACCCGTGGGTCTGGATGTAGACGTTGCACTTAGTGTTCGGGTCG
 170    GlnSerSerGlyLeuTyrSerLeuSerSerValValThrValProSerSerLeuGlyThrGlnThrTyrIleCysAsnValAsnHisLysProSer
                                                                                            sau96I
                                                                                            avaII
                       bsp1286                           alwNI                  scrFI    nlaIV
                       banII                       nlaIII bsp1286               bstNI nlaIV       mboII
 401 AACACCAAGGTGGACAAGAAAGTTGAGCCCAAATCTTGTGACAAAACTCACACATGCCCACCGTGCCCAGCACCTGAACTCCTGGGGGGACCGTCAGTCT
     TTGTGGTTCCACCTGTTCTTTCAACTCGGGTTTAGAACACTGTTTTGAGTGTGTACGGGTGGCACGGGTCGTGGACTTGAGGACCCCCCTGGCAGTCAGA
 203    AsnThrLysValAspLysLysValGluProLysSerCysAspLysThrHisThrCysProProCysProAlaProGluLeuLeuGlyGlyProSerValPhe
```

```
                                                            scrFI
                                                            bstNI
                                         scrFI       bspMI
                                         bstNI
                             fokI  alul  ncil                        scrFI
                      rsaI   fokI  alul  mspI        ncil            bstNI
         fnu4HI              ncil  mspI  hpaII       mspI            ncil           pleI         nlaIV  mboII
         bbvI  aval          mspI  hpaII smaI        hpaII           mspI   mnlI    hinfI  mnlI
801 GGCAGCCCGGAGAACCACAGGTGTACACCCTGCCCCATCCCGGGATGAGCTGACCAAGAACCAGGTCAGCCTGCTGACCTGGACCTGCTGGTCAAAGGCTTCTATCC
    CCGTCGGGCCTCTTGGTGTCCACATGTGGGACGGGGTAGGGCCCTACTCGACTGGTTCTTGGTCAGTCGGACTCGGACTGGACCTGGACCTGGACCAGTTCCGAAGATAGG
337 GlnProArgGluProValTyrThrLeuProProSerArgAspGluLeuThrLysAsnGlnValSerLeuLeuThrCysLeuValLysGlyPheTyrPro mspI
                                                     hpaII
                                                     fnu4HI
                                                     bbvI                                            nlaIII
                                                                                                     nsiI
                                                                                             mnlI    avaIII    mnlI
901 CAGCGACATCGCCCGTGGAGTGGGAGAGAGCAATGGGCAGCCGGAGAACAACTACAAGACCACGCCTCCCGTGCTGGACTCCGACGGCTCCTTCTTCCTCTAC
    GTCGCTGTAGCGGGCACTCACCCTCTCGTTACCCGTCGGCCTCTTGTTGATGTTCTGGTGCGGAGGGCACGACCTGAGGCTGCCGAGGAAGAAGGAGATG
370 SerAspIleAlaValGluTrpGlnProValGlnProGluSerAsnGlySerArgAsnTyrLysThrThrProProValLeuAspSerPheLeuTyr hphI                                                     xmnI mboII nlaIII  sfaNI    mnlI   mboII mnlI
              aluI   bspMI    fnu4HI
1001 AGCAAGCTCACCGTGGACAAGAGCAGGTGGCAGCAGGGAACGTCTCTTCATGCTCCGTGATGCATGAGGCTCTGCACAACCACTACACGCAGAAGAGCC
     TCGTTCGAGTGGCACCTGTTCTCGTCCACCGTCGTCCCTTGCAGAGAAGTACGACGGCACTACGTACTCCGAGACGTGTTGGTGATGTGCGTCTTCCGG
403  SerLysLeuThrValAspLysSerArgTrpGlnGlnGlyAsnValPheSerCysSerValMetHisGluAlaLeuHisAsnHisTyrThrGlnLysSerLeu scrFI
                ncil       mspI
                mspI       hpaII
                hpaII      haeIII
                           xmaIII
                           eaeI
1101 TCTCCCCTGTCTCCGGGTAAATGAGTGCGACGGCCG
     AGAGGGGACAGAGGCCCATTTACTCACGCTGCCGGC
437  SerLeuSerProGlyLysOP*
```

ADHESON VARIANTS

This application is a continuation application under 37 C.F.R. §1.53(b) claiming priority to co-pending application Ser. No. 09/641,554, filed on Aug. 17, 2000 now abandoned, which is a continuation of application Ser. No. 09/275,310, filed on Mar. 24, 1999, now abandoned which is a continuation of application Ser. No. 08/457,918, filed on Jun. 1, 1995 (U.S. Pat. No. 6,117,655), which is a continuation of application Ser. No. 08/236,311, filed on May 2, 1994 (U.S. Pat. No. 5,565,335), which is a continuation of application Ser. No. 07/936,190, filed on Aug. 26, 1992 (U.S. Pat. No. 5,336,603), which is a divisional of application Ser. No. 07/842,777 filed on Feb. 18, 1992 (now abandoned), which is a continuation of application Ser. No. 07/250,785, filed Sep. 28, 1988 (now abandoned) which is a continuation-in-part of application Ser. No. 07/104,329, filed Oct. 2, 1987 (now abandoned) which applications are incorporated herein by reference.

BACKGROUND OF THE INVENTION

This application relates to compositions for antiviral or immunomodulatory therapy. In particular, it relates to compositions useful in the treatment of Human Immunodeficiency Virus (HIV) infections.

The primary immunologic abnormality resulting from infection by HIV is the progressive depletion and functional impairment of T lymphocytes expressing the CD4 cell surface glycoprotein (H. Lane et al., Ann. Rev. Immunol. 3:477 [1985]). CD4 is a non-polymorphic glycoprotein with homology to the immunoglobulin gene superfamily (P. Maddon et al., Cell 42:93 [1985]). Together with the CD8 surface antigen, CD4 defines two distinct subsets of mature peripheral T cells (E. Reinherz et al., Cell 19:821 [1980]), which are distinguished by their ability to interact with nominal antigen targets in the context of class I and class II major histocompatibility complex (MHC) antigens, respectively (S. Swain, Proc. Natl. Acad. Sci. 78:7101 [1981]; E. Engleman et al., J. Immunol. 127:2124 [1981]; H. Spitz et al., J. Immunol. 129:1563 [1982]; W. Biddison et al., J. Exp. Med. 156:1065 [1982]; and D. Wilde et al., J. Immunol. 131:2178 [1983]). For the most part, CD4 T cells display the helper/inducer T cell phenotype (E. Reinherz, supra), although CD4 T cells characterized as cytotoxic/suppressor T cells have also been identified (Y. Thomas et al., J. Exp. Med. 154:459 [1981]; S. Meuer et al., Proc. Natl. Acad. Sci. USA 79:4395 [1982]; and A. Krensky et al., Proc. Natl. Acad. Sci. USA 79:2365 [1982]). The loss of CD4 helper/inducer T cell function probably underlies the profound defects in cellular and humoral immunity leading to the opportunistic infections and malignancies characteristic of the acquired immunodeficiency syndrome (AIDS) (H. Lane supra).

Studies of HIV-I infection of fractionated CD4 and CD8 T cells from normal donors and AIDS patients have revealed that depletion of CD4 T cells results from the ability of HIV-I to selectively infect, replicate in, and ultimately destroy this T lymphocyte subset (D. Klatzmann et al., Science 225:59 [1984]). The possibility that CD4 itself is an essential component of the cellular receptor for HIV-I was first indicated by the observation that monoclonal antibodies directed against CD4 block HIV-I infection and syncytia induction (A. Dalgleish et al., Nature [London] 312:767 [1984]; J. McDougal et al., J. Immunol. 135:3151 [1985]). This hypothesis has been confirmed by the demonstration that a molecular complex forms between CD4 and gp120, the major envelope glycoprotein of HIV-I (J. McDougal et al., Science 231:382 [1986]; and the finding that HIV-I tropism can be conferred upon ordinarily non-permissive human cells following the stable expression of a CD4 cDNA (P. Maddon et al., Cell 47:333 [1986]). Furthermore, the neurotropic properties of HIV-I, reflected by a high incidence of central nervous system dysfunction in HIV-I infected individuals (W. Snider et al., Ann. Neurol. 14:403 [1983]), and the ability to detect HIV-I in the brain tissue and cerebrospinal fluid of AIDS patients (G. Shaw et al., Science 227:177 [1985]; L. Epstein, AIDS Res. 1:447 [1985]; S. Koenig, Science 233:1089 [1986]; D. Ho et al., N. Engl. J. Med. 313:1498 [1985]; J. Levy et al., Lancet II:586 [1985]), appears to have its explanation in the expression of CD4 in cells of neuronal, glial and monocyte/macrophage origin (P. Maddon, Cell 47:444 [1986]; I. Funke et al., J. Exp. Med. 165:1230 [1986]; B. Tourvieille et al., Science 234:610 [1986]).

In addition to determining the susceptibility to HIV-I infection, the manifestation of cytopathic effects in the infected host cell appears to involve CD4. Antibody to CD4 was found to inhibit the fusion of uninfected CD4 T cells with HIV-I infected cells in vitro; moreover, the giant multinucleated cells produced by this event die shortly after being formed resulting in the depletion of the population of CD4 cells (J. Lifson et al., Science 232:1123 [1986]). Formation of syncytia also requires gp120 expression, and can be elicited by coculturing CD4-positive cell lines with cell lines expressing the HIV-I env gene in the absence of other viral structural or regulatory proteins (J. Sodroski et al., Nature 322:470 [1986]; J. Lifson et al., Nature 323:725 [1986]). Thus, in mediating both the initial infection by HIV-I as well as eventual cell death, the interaction between gp120 and CD4 constitutes one of several critical entry points in the viral life cycle amenable to therapeutic intervention (H. Mitsuya et al., Nature 325:773 [1987]).

The known sequence of the CD4 precursor predicts a hydrophobic signal peptide, an extracellular region of approximately 370 amino acids, a highly hydrophobic stretch with significant identity to the membrane-spanning domain of the class II MHC beta chain, and a highly charged intracellular sequence of 40 residues (P. Madden, Cell 42:93 [1985]). The extracellular domain of CD4 consists of four contiguous regions each having amino acid and structural similarity to the variable and joining (V–J) domains of immunoglobulin light chains as well as related regions in other members of the immunoglobulin gene superfamily (a subclass of which are defined herein by the coined term "adhesons". These structurally similar regions of CD4 are termed the $V_1$, $V_2$, $V_3$ and $V_4$ domains (denominated 1–4 in FIG. 3).

A successful strategy in the development of drugs for the treatment of many receptor mediated abnormalities has been the identification of antagonists which block binding of the natural ligand. Since the CD4 adheson ordinarily binds to the recognition sites of the HIV envelope it would appear to be a candidate for therapeutically sequestering these HIV sites, thereby blocking viral infectivity. However, full length CD4 and other adhesons are cell membrane proteins which are anchored in the lipid bilayer of cells. The presence of membrane components will be undesirable from the standpoint of manufacturing and purification. In addition, since adhesons are normally present only on cell surfaces, it would be desirable to produce adhesons in a form which is more stable in the circulation. Additionally, even truncated, soluble CD4 adheson (generally referred to as CD4T) may not be optimally effective as a therapeutic since it possesses a relatively short biological half-life, binds to HIV no better than cell surface CD4, may not cross the placental or other biological barriers and since it merely sequesters the HIV recognition sites without in itself bearing an infected-cell killing or virus killing functionality.

Accordingly, it is an object of this invention to produce soluble, secreted adhesons. It is another object to produce CD4 derivatives useful in the treatment of AIDS and related conditions, in a manner essentially unaffected by the extreme degree of genetic variation observed among various HIV-I isolates and their respective env polypeptides (J. Coffin, Cell 46:1 [1986]). Still another object is to prepare adhesons fused to other polypeptides in order to provide molecules with novel functionalities such as those described above for therapeutic use, or diagnostic reagents for the in vitro assay of adhesons or their ligands. In particular, it is an objective to prepare molecules for directing toxins or effector molecules (for example the Fc domain of immunoglobulin) to cells bearing receptors for the adhesons, e.g. HIV gp120 in the case of CD4, and for use in facilitating purification of the adhesons. It is a further object to provide stable, highly purified adheson preparations.

SUMMARY

The objects of this invention are accomplished by providing nucleic acid encoding an amino acid sequence variant of an adheson, in particular a variant in which the transmembrane domain is modified so that it is no longer capable of becoming lodged in the cell membrane. In the case of CD4 such variants are termed soluble CD4.

Variant adhesons are produced by a method comprising (a) transforming a host cell with nucleic acid encoding an amino acid sequence variant of an adheson, (b) culturing the host cell and (c) recovering the variant adheson from the host cell culture media or from lysates of the host cell.

In specific embodiments, the objects of this invention are accomplished by providing an adheson variant selected from the group consisting of (a) an adheson amino acid sequence variant having an inactivated transmembrane domain and (b) a polypeptide comprising an adheson extracellular domain fused to the sequence of a polypeptide which is different from the adheson, this latter, for example, selected from a cytotoxin, an immunogen or a protein with a long plasma half life such as an immunoglobulin constant domain.

In a preferred embodiment a polypeptide comprising a gp120 binding domain of the CD4 adheson is fused at its C-terminus to an immunoglobulin constant domain, or is linked to a cytotoxic polypeptide such as ricin.

The CD4 adheson variants provided herein are purified and formulated in pharmacologically acceptable vehicles for administration to patients in need of antiviral, neuromodulatory or immunomodulatory therapy, in particular patients infected with HIV, and for use in the modulation of cell adhesion.

BRIEF DESCRIPTION OF THE DRAWINGS

FIGS. 1a–1c depict the amino acid and nucleotide sequence of a secreted form of the CD4 adheson. The signal processing site is designated with an arrow.

Figure 2A:
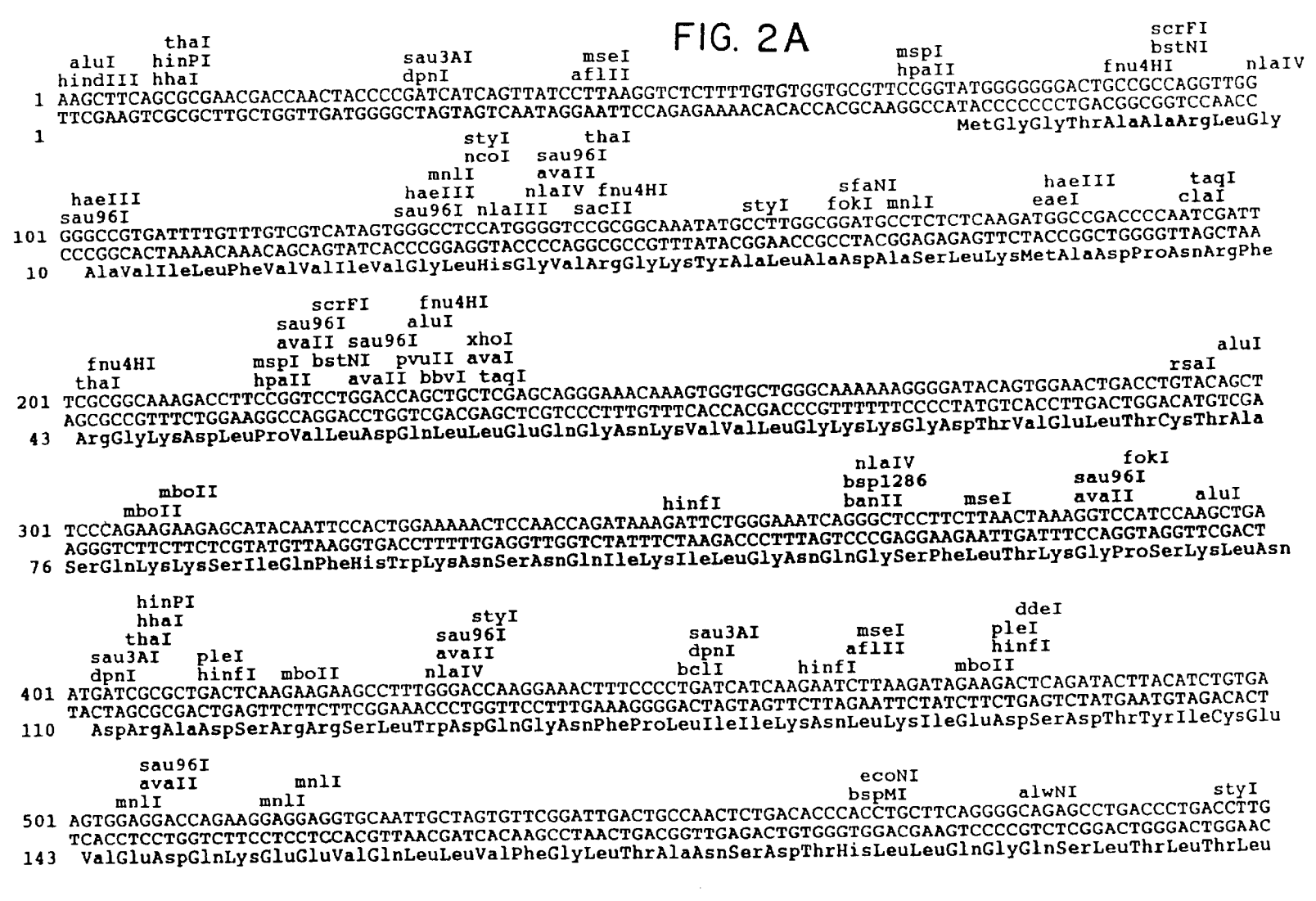

FIGS. 2a–2c depict the amino acid and nucleotide sequence of a fusion of the herpes gD leader and N-terminal 27 residues to the putative mature N-terminus of CD4T.

Figure 4B-1:
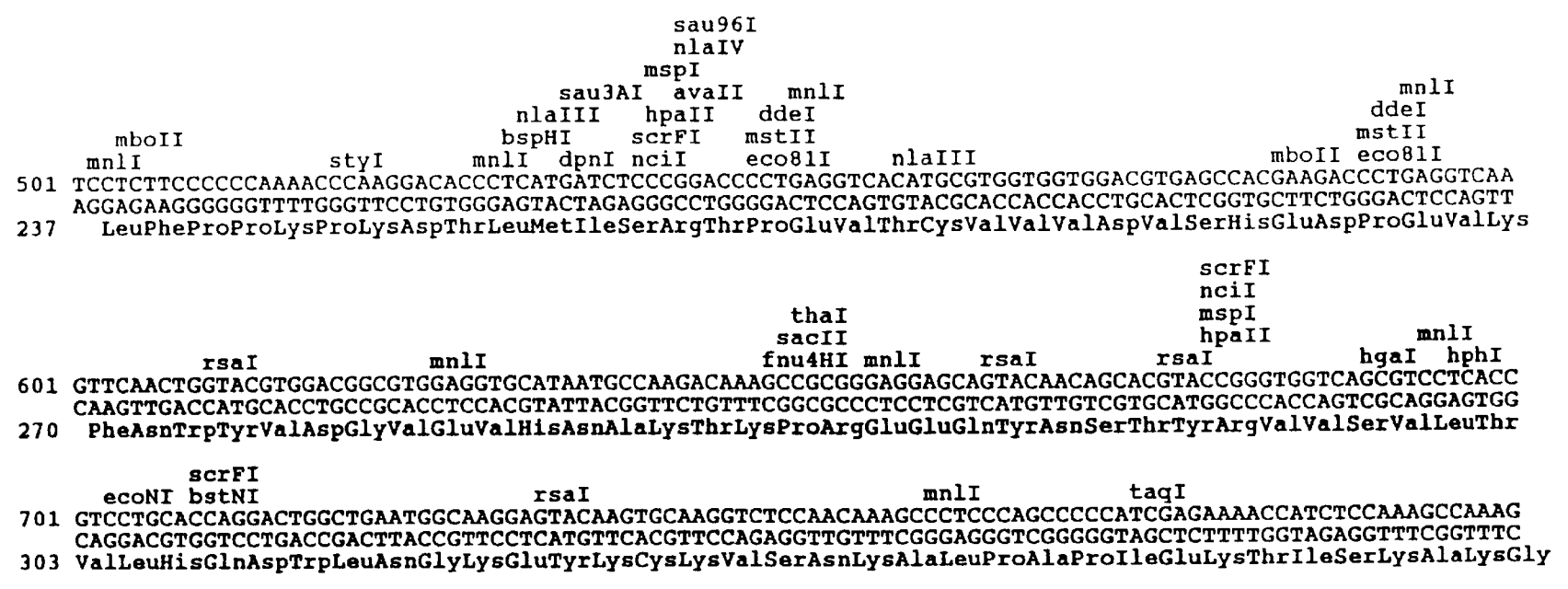

FIGS. 4A–4B–2 are a map of the linkered human $IgG_1$ ($\gamma_1$) chain fragment employed in the preparation of CD4 fusions. Insert sites are designated γ1 and Fc.

FIG. 5 is a map of the human κ light chain fragment useful for CD4 fusions at the arrow flanked by $V_\kappa J_\kappa$ (light variable and joining) and $C_\kappa$ (light constant).

DETAILED DESCRIPTION

Figure 3:
FIG. 3 depicts the structural elements of the native and soluble CD4 adheson, the native human $IgG_1$ ($\gamma_1$) heavy chain and two exemplary heavy chain-CD4 chimeras.
Figure 3:
Figure 3:
Figure 3:
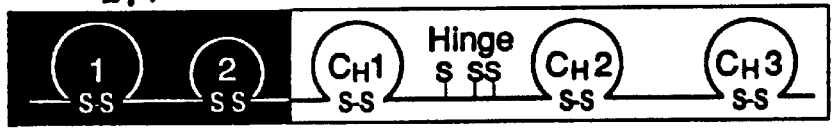
Figure 3:

Adhesons are cell surface polypeptides having an extracellular domain which is homologous to a member of the immunoglobulin gene superfamily, excluding, however, highly polymorphic members of this superfamily selected from the group of class I and class II major histocompatibility antigens, immunoglobulins and T-cell receptor α, β, γ and δ chains. Examples of adhesons include CD1, CD2, CD4, CD8, CD28, the γ, δ and ε chains of CD3, OX-2, Thy-1, the intercellular or neural cell adhesion molecules (I-CAM or N-CAM), lymphocyte function associated antigen-3 (LFA-3), neurocytoplasmic protein (NCP-3), poly-Ig receptor, myelin-associated glycoprotein (MAG), high affinity IgE receptor, the major glycoprotein of peripheral myelin (Po), platelet derived growth factor receptor, colony stimulating factor-1 receptor, macrophage Fc receptor, Fc gamma receptors and carcinoembryonic antigen. Homologous as defined herein means having the sequence of a member of the immunoglobulin gene superfamily or having a sequence therewithin which has substantially the same as (or a greater degree of) amino acid sequence homology to a known member of the superfamily as the specific examples given above have to the sequence of an immunoglobulin variable or constant domain. Preferred adhesons are CD4, CD8 and high affinity IgE Fc receptor.

This invention is particularly concerned with amino acid sequence variants of adhesons. Amino acid sequence variants of adhesons are prepared with various objectives in mind, including increasing the affinity of the adheson for its binding partner, facilitating the stability, purification and preparation of the adheson, increasing its plasma half life, improving therapeutic efficacy as described above in the background, introducing additional functionalities and lessening the severity or occurrence of side effects during therapeutic use of the adheson. Amino acid sequence variants of adhesons fall into one or a combination of the following classes: insertional, substitutional or deletional variants.

Insertional amino acid sequence variants are those in which one or more amino acid residues extraneous to the adheson are introduced into a predetermined site in the adheson including the C or N termini. Such variants are referred to as fusions of the adheson and a different polypeptide. Such other polypeptides contain sequences other than those which are normally found in the adheson at the inserted position. Several groups of fusions are contemplated herein. Immunologically active adheson fusions comprise an adheson and a polypeptide containing a non-adheson epitope. The non-adheson epitope is any immunologically competent polypeptide, i.e., any polypeptide which is capable of eliciting an immune response in the animal to which the fusion is to be administered or which is capable of being bound by an antibody raised against the non-adheson polypeptide. Typical non-adheson epitopes will be those which are borne by allergens, autoimmune epitopes, or other potent immunogens or antigens recognized by pre-existing antibodies in the fusion recipient, including bacterial polypeptides such as trpLE, betagalactosidase, viral polypeptides such as herpes gD protein, and the like. Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into the adheson antigen or fragment thereof by a peptide bond(s). These products therefore consist of a linear polypeptide chain containing adheson epitopes and at least one epitope foreign to the adheson. It will be understood that it is within the scope of this invention to introduce the epitopes anywhere within the adheson molecule or fragment thereof. Such fusions are conveniently made in recombinant host cells or by the use of bifunctional cross-linking agents. The use of a cross-linking agent to fuse the adheson to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against the adheson, which antibodies in turn are useful in diagnostics or in purification of adheson by immunoaffinity techniques known per se. Alternatively, in the purification of adhesons, binding partners for the fused non-adheson polypeptide, e.g. antibodies, receptors or ligands, are used to adsorb the fusion from impure admixtures, after which the fusion is eluted and, if desired, the adheson is recovered from the fusion, e.g. by enzymatic cleavage.

Other fusions, which may or may not also be immunologically active, include fusions of the adheson sequence with a signal sequence heterologous to the adheson, fusions of transmembrane-modified CD4 adhesons, for example, to polypeptides having enhanced plasma half life (ordinarily>about 20 hours) such as immunoglobulin chains or fragments thereof, and fusions with cytotoxic functionalities. Signal sequence fusions are employed in order to more expeditiously direct the secretion of the adheson. The heterologous signal replaces the native adheson signal, and when the resulting fusion is recognized, i.e. processed and cleaved by the host cell, the adheson is secreted. Signals are selected based on the intended host cell, and may include bacterial yeast, mammalian and viral sequences. The herpes gD glycoprotein signal is suitable for use in mammalian expression systems.

Plasma proteins which have enhanced plasma half-life longer than that of transmembrane modified CD4 include serum albumin, immunoglobulins, apolipoproteins, and transferrin. Preferably, the adheson-plasma protein fusion is not significantly immunogenic in the animal in which it is used and the plasma protein does not cause undesirable side effects in patients by virtue of its normal biological activity.

In a specific embodiment the adheson immunoglobulin-like domain which may be homologous either to the constant or to the variable region domains is conjugated with an immunoglobulin constant region sequence. The resulting products are referred to herein as immunoadhesons. Immunoglobulins and certain variants thereof are known and many have been prepared in recombinant cell culture. For example, see U.S. Pat. No. 4,745,055; EP 256,654; Faulkner et al., Nature 298:286 (1982); EP 120,694; EP 125,023; Morrison, J. Immun. 123:793 (1979); Köhler et al., P.N.A.S. USA 77:2197 (1980); Raso et al., Cancer Res. 41:2073 (1981); Morrison et al., Ann. Rev. Immunol. 2:239 (1984); Morrison, Science 229:1202 (1985); Morrison et al., P.N.A.S. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein.

Ordinarily, the domains of adhesons that are homologous to immunoglobulins and extracellular in their native environment are fused C-terminally to the N-terminus of the constant region of immunoglobulins in place of the variable region(s) thereof, retaining at least functionally active hinge, CH2 and CH3 domains of the constant region of an immunoglobulin heavy chain. This ordinarily is accomplished by constructing the appropriate DNA sequence and expressing it in recombinant cell culture. Immunoglobulins and other polypeptides having enhanced plasma half life are fused to the extracellular or ligand binding domains of other adhesons in the same fashion.

The boundary domains for the CD4 V-like regions (V1–V4) are, respectively, about 100–109, about 175–184, about 289–298, and about 360–369 (based on the precursor CD4 amino acid sequence in which the initiating met is –25; FIG. 1a). CD4 sequences containing any of the CD4 V domains are fused to the immunoglobulin sequence. It is preferable that the V1V2 or V1V2V3V4 be fused at their C-termini to the immunoglobulin constant region. The precise site at which the fusion is made is not critical; the boundary domains noted herein are for guidance only and other sites neighboring or within the V regions may be selected in order to optimize the secretion or binding characteristics of the CD4. The optimal site will be determined by routine experimentation. In general, it has been found that the fusions are expressed intracellularly, but a great deal of variation is encountered in the degree of secretion of the fusions from recombinant hosts. For instance, the following table demonstrates the various immunoglobulin fusions that have been obtained by the method of this invention. In all examples of CD4 immunoadhesons, the CD4 signal was used to direct secretion from 293 cells. Lower case m represents murine origin, while the lower case h designates human origin. V and C are abbreviations for immunoglobulin variable and constant domains respectively. The numerical subscripts indicate the number of parenthetical units found in the designated multimer. It will be understood that the chains of the multimers are believed to be disulfide bonded in the same fashion as native immunoglobulins. The CD4 immunoadhesons typically contained either the first N-terminal 366 residues of CD4 ($CD4_4$) or the first 180 N-terminal residues of CD4 ($CD4_2$) linked at their C-terminus to the κ (light) chain or IgG1 heavy chain constant region (γ1).

TABLE I

| Transfected Gene | Secreted Product |
| --- | --- |
| $mV_\kappa C_\kappa$ | $mV_\kappa C_\kappa$ and/or $(mV_\kappa C_\kappa)_2$ |
| $mV_{\gamma 1} C_{\gamma 1}$ | ND |
| $mV_\kappa C_\kappa + mV_{\gamma 1} C_{\gamma 1}$ | $(mV_\kappa C_\kappa)_2 (mV_{\gamma 1} C_{\gamma 1})_2 +$ $mV_\kappa C_\kappa$ and/or $(mV_\kappa C_\kappa)_2$ |
| $hCD4-mC_\kappa$ | $hCD4-mC_\kappa$ and/or $(hCD4-mC_\kappa)_2$ |
| $hCD4-mC_{\gamma 1}$ | ND |
| $hCD4-mC_\kappa + hCD4-mC_{\gamma 1}$ | $(hCD4-mC_\kappa)_2 (hCD4-mC_{\gamma 1})_2 +$ $hCD4-mC_\kappa$ and/or $(hCD4-mC_\kappa)_2$ |
| $hCD4-hC_\kappa$ | $hCD4-hC_\kappa$ and/or $(hCD4-hC_\kappa)_2$ |
| $hCD4-hC_{\gamma 1}$ | $(hCD4-hC_{\gamma 1})_2$ |
| $hCD4-hC_\kappa + hCD4-hC_{\gamma 1}$ | $(hCD4-hC_\kappa)_2 (hCD4-hC_{\gamma 1})_2 +$ $hCD4-hC_\kappa$ and/or $(hCD4-hC_\kappa)_2$ |
| $mV_\kappa C_\kappa + hCD4-hC_{\gamma 1}$ | $(mV_\kappa C_\kappa)_2 (hCD4-hC_{\gamma 1})_2 +$ $mV_\kappa C_\kappa$ and/or $(mV_\kappa C_\kappa)_2$ |

* ND = Not detected

It is interesting to observe from this table that the CD4-human heavy chain immunoadheson was secreted as a dimer whereas the analogous murine construction was not detected (this not excluding the intracellular accumulation of the protein, however). The ability of the hCD4-hCγ1 transformants to produce heavy chain dimer was unexpected since previous work had suggested that immunoglobulin heavy chains are not secreted unless the hosts are cotransformed with nucleic acid encoding both heavy and light chain (Valle et al., *Nature* 241:338 [1981]). According to this invention, CD4-IgG immunoadheson chimeras are readily secreted wherein the CD4 epitope is present in heavy chain dimers, light chain monomers or dimers, and heavy and light chain heterotetramers wherein the CD4 epitope is present fused to one or more light or heavy chains, including heterotetramers wherein up to and including all four variable region analogues are derived from CD4. Where light-heavy chain non-CD4 variable domain is present, a heterofunctional antibody thus is provided.

Various exemplary hetero- and chimeric immunoadheson antibodies produced in accordance with this invention are schematically diagrammed below. "A" means at least a portion of the extracellular domain of an adheson containing its ligand binding site; $V_L$, $V_H$, $C_L$ and $C_H$ represent light or heavy chain variable or constant domains of an immunoglobulin; n is an integer; and Y designates a covalent cross-linking moiety.

(a) $AC_L$;
(b) $AC_L$-$AC_L$;
(c) $AC_H$-[$AC_H$, $AC_L$-$AC_H$, $AC_L$-$V_H C_H$, $V_L C_L$-$AC_H$, or $V_L C_L$-$V_H C_H$];
(d) $AC_L$-$AC_H$-[$AC_H$, $AC_L$-$AC_H$, $AC_L$-$V_H C_H$, $V_L C_L$-$AC_H$, or $V_L C_L$-$V_H C_H$];
(e) $AC_L$-$V_H C_H$-[$AC_H$, $AC_L$-$AC_H$, $AC_L$-$V_H C_H$, $V_L C_L$-$AC_H$, or $V_L C_L$-$V_H C_H$];
(f) $V_L C_L$-$AC_H$-[$AC_H$, $AC_L$-$AC_H$, $AC_L$-$V_H C_H$, $V_L C_L$-$AC_H$, or $V_L C_L$-$V_H C_H$]; or
(g) $[A-Y]_n$-$[V_L C_L$-$V_H C_H]_2$.

The structures shown in this table show only key features, e.g. they do not show joining (J) or other domains of the immunoglobulins, nor are disulfide bonds shown. These are omitted in the interests of brevity. However, where such domains are required for binding activity they shall be construed as being present in the ordinary locations which they occupy in the adheson, immunoadheson or immunoglobulin molecules as the case may be. These examples are representative of divalent antibodies; more complex structures would result by employing immunoglobulin heavy chain sequences from other classes, e.g. IgM. The immunoglobulin $V_L V_H$ antibody combining site also designated as the companion immunoglobulin, preferably is capable of binding to a predetermined antigen.

Suitable companion immunoglobulin combining sites and fusion partners are obtained from IgG-1, -2, -3, or -4 subtypes, IgA, IgE, IgD or IgM, but preferably IgG-1.

A preferred embodiment is a fusion of an N-terminal portion of CD4, which contains the binding site for the gp120 envelope protein of HIV, to the C-terminal $F_c$ portion of an antibody, containing the effector functions of immunoglobulin $G_1$. There are two preferred embodiments of this sort; in one, the entire heavy chain constant region is fused to a portion of CD4; in another, a sequence beginning in the hinge region just upstream of the papain cleavage site which defines IgG $F_c$ chemically (residue 216, taking the first residue of heavy chain constant region to be 114 [Kobat et al., "Sequences of Proteins of Immunological Interest" 4th Ed., 1987], or analogous sites of other immunoglobulins) is fused to a portion of CD4. These embodiments are described in the examples.

More particularly, those variants in which one or more immunoglobulin-like domains of an adheson are substituted for the variable region of an immunoglobulin chain are believed to exhibit improved in vivo plasma half life. These chimeras are constructed in a fashion similar to chimeric antibodies in which a variable domain from an antibody of one species is substituted for the variable domain of another species. See, for example, EP 0 125 023; Munro, Nature 312: (Dec. 13, 1984); Neuberger et al., Nature 312: (Dec. 13, 1984); Sharon et al., Nature 309: (May 24, 1984); Morrison et al., Proc. Natl. Acad. Sci. USA 81:6851–6855 (1984); Morrison et al. Science 229:1202–1207 (1985); and Boulianne et al., Nature 312:643–646 (Dec. 13, 1984). The DNA encoding the adheson immunoglobulin-like domain(s) is cleaved by a restriction enzyme at or proximal to the 3' end of the DNA encoding the immunoglobulin-like domain(s) and at a point at or near the DNA encoding the N-terminal end of the mature adheson polypeptide (where use of a different leader is contemplated) or at or proximal to the N-terminal coding region for the adheson (where the native adheson signal is employed). This DNA fragment then is readily inserted into DNA encoding an immunoglobulin light or heavy chain constant region and, if necessary, tailored by deletional mutagenesis. Preferably, this is a human immunoglobulin when the variant is intended for in vivo therapy for humans. DNA encoding immunoglobulin light or heavy chain constant regions is known or readily available from cDNA libraries or is synthesized. See for example, Adams et al., Biochemistry 19:2711–2719 (1980); Gough et al., Biochemistry 19:2702–2710 (1980); Dolby et al., P.N.A.S. USA, 77:6027–6031 (1980); Rice et al., P.N.A.S. USA 79:7862–7865 (1982); Falkner et. al., Nature 298:286–288 (1982); and Morrison et al., Ann. Rev. Immunol. 2:239–256 (1984).

DNA encoding the immunoglobulin or immunoadheson chimeric chain(s) is transfected into a host cell for expression. If the host cell is producing an immunoglobulin prior to transfection then one need only transfect with the adheson fused to light or to heavy chain to produce a heteroantibody. The aforementioned immunoglobulins having one or more arms bearing the adheson domain and one or more arms bearing companion variable regions result in dual specificity for adheson ligand and for an antigen. These are produced by the above-described recombinant methods or by in vitro procedures. In the latter case, for example, $F(ab')_2$ fragments of the adheson fusion and an immunoglobulin are prepared, the $F(ab')_2$ fragments converted to Fab' fragments by reduction under mild reducing conditions, and then reoxidized in each other's presence under acidic conditions in accord with methods known per se. See also U.S. Pat. No. 4,444,878. Additionally, procedures are known for producing intact heteroantibodies from immunoglobulins having different specificities. These procedures are adopted for the in vitro production of heterochimeric antibodies by simply substituting the immunoadheson chains for one of the previously employed immunoglobulins.

In an alternative method for producing a heterofunctional antibody, host cells producing an adheson-immunoglobulin fusion, e.g. transfected myelomas, also are fused with B cells or hybridomas which secrete antibody having the desired companion specificity for an antigen. Heterobifunctional antibody is recovered from the culture medium of such hybridomas, and thus may be produced somewhat more conveniently than by conventional in vitro resorting methods (EP 68,763).

Another group of fusions are those in which an adheson is conjugated with a toxic substance, e.g. a polypeptide such as ricin (including deglycosylated ricin A chain), diptheria toxin A, or a non-peptidyl cytotoxin. Where the toxin is a polypeptide it is convenient to cross-link the polypeptide to the adheson or its transmembrane-deleted variant by conventional in vitro protein cross-linking agents (for suitable methods for linking ricin A chain or deglycosylated A chain to CD4 see, for example, Duncan et al., "Analy. Biochem." 132:68–73 [1983]; Thorpe et al., "Cancer Res." 47:5924 [1987]; and Ghotie et al., "Cancer Res." 48:2610 [1988]) or by recombinant synthesis as a fusion (see for example, U.S. Pat. No. 4,765,382). Alternatively, where companion antibodies are anti-ricin antibody immunoglobulin variable domains, such immunoglobulin heteroantibodies are employed to deliver ricin to HIV infected cells following the general procedure of Raso et al., Cancer Research, 41:2073 (1981).

Another class of adheson variants are deletional variants. Deletions are characterized by the removal of one or more amino acid residues from a adheson sequence. Typically, the transmembrane and cytoplasmic domains of adhesons ar deleted. In the case of CD4, at least residues 368 to 395 (the transmembrane region), and ordinarily 396–433 as well (the cytoplasmic domain), will be deleted to obtain secreted forms of this adheson. Parenthetically, the amino acid residues follow the numbers given for mature CD4 as noted, for example, in FIGS. 1a–1c. Thus, CD4T molecules generally will terminate in the vicinity of about residues 366–368, or at any other suitable site N-terminal thereto which preserves the gp120-binding capability of the CD4 variant.

Substitutional variants are those in which at least one residue in the adheson sequence has been removed and a different residue inserted in its place. The native N-terminal residue for mature CD4 is now known to be lysine. Thus, the sequence shown in FIG. 1, with an N-terminal asparagine, is an amino acid sequence variant of native mature CD4. Table 2 below describes substitutions which in general will result in fine modulation of the characteristics of the CD antigen.

TABLE 2

| Original Residue | Exemplary Substitutions |
|---|---|
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in adheson properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteinyl or prolyl is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanyl, is substituted for (or by) one not having a side chain, e.g., glycyl.

A preferred class of substitutional or deletional variants are those involving the transmembrane region of the adheson. The transmembrane region of the adheson is a highly hydrophobic or lipophilic domain that is the proper size to span the lipid bilayer of the cellular membrane. It is believed to anchor the adheson in the cell membrane.

Deletion or substitution of the transmembrane domain will facilitate recovery and provide a soluble form of the adheson by reducing its cellular or membrane lipid affinity and improving its water solubility. If the transmembrane and cytoplasmic domains are deleted one avoids the introduction of potentially immunogenic epitopes, either by exposure of otherwise intracellular polypeptides that might be recognized by the body as foreign or by insertion of heterologous polypeptides that are potentially immunogenic. A principal advantage of the transmembrane deleted adheson is that it is secreted into the culture medium of recombinant hosts. This variant is water soluble and does not have an appreciable affinity for cell membrane lipids, thus considerably simplifying its recovery from recombinant cell culture.

It will be amply apparent from the foregoing discussion that substitutions, deletions, insertions or any combination thereof are introduced to arrive at a final construct. As a general proposition, all variants will not have a functional transmembrane domain and preferably will not have a functional cytoplasmic sequence. This is generally accomplished by deletion of the relevant domain, although adequate insertional or substitutional mutagens also can be effective for this purpose. For example, the transmembrane domain is substituted by any amino acid sequence, e.g. a random or homopolynucleic sequence of about 5 to 50 serine, threonine, lysine, arginine, glutamine, aspartic acid and like hydrophilic residues, which altogether exhibit a hydrophilic hydropathy profile, so that it is secreted into the culture medium of recombinant hosts. This variant should also be considered to be an adheson variant.

These variants ordinarily are prepared by site specific mutagenesis of nucleotides in the DNA encoding the adheson, thereby producing DNA encoding the variant, and thereafter expressing the DNA in recombinant cell culture. However, variant adhesons also are prepared by in vitro synthesis. Obviously, variations made in the DNA encoding the variant adhesons must not place the sequence out of reading frame and preferably will not create complementary regions that could produce secondary mRNA structure deleterious to expression (EP 75,444A). The CD4 variants typically exhibit the same gp120 binding activity as does the naturally-occurring prototype, although variants also are selected in order to modify the characteristics of the CD4 adheson as indicated above.

While the site for introducing an amino acid sequence variation is predetermined, the mutation per se need not be predetermined. For example, in order to optimize the performance of a mutation at a given site, random mutagenesis may be conducted at the target codon or region and the expressed adheson variants screened for the optimal combination of desired activities. Techniques for making substitution mutations at predetermined sites in DNA having a known sequence are well known, for example M13 primer mutagenesis.

Adheson variants that are not capable of binding HIV gp120 are useful nonetheless as immunogens for raising antibodies to the adheson or as immunoassay kit components (labelled, as a competitive reagent for gp120 assay, or unlabelled as a standard for an adheson assay) so long as at least one adheson epitope remains active.

The DNA encoding adhesons is obtained by known procedures. See Williams, Immunol. Today 8:298 regimes. The first category is based on a cell's metabolism and the use of a mutant cell line which lacks the ability to grow independent of a supplemented medium. Two examples are: CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol. Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred host cells for expressing the CD antigen variants of this invention are mammalian cell lines, examples including: monkey kidney CV1 line transformed by SV40 (COS-7, ATCC CRL 1651); human embryonic kidney line (293, Graham, F. L. et al., J. Gen Virol. 36: 59 [1977] and 293S cells [293 subclones selected for better suspension growth]); baby hamster kidney cells (BHK, ATCC CCL 10); chinese hamster ovary-cells-DHFR(CHO, Urlaub and Chasin, Proc- .Natl.Acad.Sci. (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51 cells); and TRI cells (Mather, J. P. et al., Annals N.Y. Acad. Sci. 383: 44–68 [1982]).

"Transformation" means introducing DNA into an organism so that the DNA is replicable, either as an extrachromosomal element or by chromosomal integration. One suitable for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell walls are used as hosts, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employ standard and manipulative ligation techniques. Isolated plasmids or DNA fragments are cleaved, tailored, and religated in the form desired to form the plasmids required. Suitable procedures are well known for the construction described herein. See, for example, (Maniatis, T. et al., *Molecular Cloning*, 133–134 Cold Spring Harbor, [1982]; "Current Protocols in Molecular Biology", edited by Ausubel et al., [1987], pub. by Greene Publishing Associates & Wiley-Interscience).

Correct plasmid sequences are confirmed by transforming *E. coli* K12 strain 294 (ATCC 31446) with ligation mixtures, successful transformants selected by ampicillin or tetracycline resistance where appropriate, plasmids from the transformants prepared, and then analyzed by restriction enzyme digestion and/or sequenced by the method of Messing et al., Nucleic Acids Res. 9: 309 (1981) or by the method of Maxam et al., Methods in Enzymology 65: 499 (1980).

Host cells are transformed with the expression vectors of this invention. Thereafter they are cultured in appropriate culture media, e.g. containing substances for inducing promoters, selecting transformants or amplifying genes. The culture conditions, such as temperature, pH and the like, are those previously used with the host cell selected for expression, and will be apparent to the ordinarily skilled artisan.

The secreted adheson variants are recovered and purified from the culture supernatants or lysates of recombinant hosts. Typically, the supernatants are concentrated by ultrafiltration, contacted with a ligand affinity or immunoaffinity matrix so as to adsorb the adheson variant, and eluted from the matrix. Optionally, the adheson is purified by ion exchange chromatography.

Surprisingly, purification of soluble CD4 adheson from culture medium was unexpectedly difficult. Notwithstanding that the hydrophobic transmembrane region of the antigen had been deleted, the antigen exhibited a strong tendency to form aggregates that could be readily removed from suspension by centrifugation at 1000× g, and which avidly coat surfaces such as ultrafiltration membranes. This appears to result from the reduction in concentration of albumin or other serum protein (ordinarily present in the crude preparation) to a particular level, below which the truncated antigen no longer remains soluble. This phenomenon appears to be aggravated by exposure of the CD4 adheson to low pH (<about pH 4). As a result, separation procedures (particularly those that employ acid elution, such as immunoaffinity) should be modified so that the eluate is maintained at, or immediately returned to, about neutrality. Further, a surfactant, e.g. a detergent such as Tween 80, should be included with the antigen during the separation procedure. The final purified product will be stabilized with a predetermined protein such as albumin, and/or a detergent.

The purified adheson is formulated into conventional pharmacologically acceptable excipients.

It is administered to patients having HIV infection at a dosage capable of maintaining a concentration of greater than about 100 ng of soluble CD4 adheson/ml plasma. For CD4 adheson variants having different molecular weights, about 2 picomoles of soluble receptor per ml of plasma will be initially evaluated clinically in order to establish a stoichiometric equivalence with native (membrane bound) and soluble receptor. The ordinary dosage of soluble CD4 is 100 µg/kg of patient weight/day.

The therapeutic CD4 variants are employed with other therapies and agents for the treatment of AIDS, including AZT, neutralizing antibodies and immunocytotoxins, gp120 fragments and vaccines.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103–6114 [1981], and Goeddel, D. et al., Nucleic Acids Res. 8: 4057 [1980]).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation and other recombinant manipulations are conventional. Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Ligation" refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 µg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 µg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase 1 and 250 µM of each of the four deoxynucleoside triphosphates. The incubation generally is terminated after 30 min. phenol and chloroform extraction and ethanol precipitation.

The following examples merely illustrate the best mode now contemplated for practicing the invention, but should not be construed to limit the invention. All literature citations herein are expressly incorporated by reference.

EXAMPLE 1

Construction of Vectors for the Expression of Native CD4 and Secreted Derivatives Section 1

The plasmid used for recombinant synthesis of human CD4 was pSVeCD4DHFR. The plasmid was constructed as follows:

λCD4P1 containing most of the coding sequence of human CD4 (obtained from a human placental cDNA library using oligonucleotide probes based on the published sequence [Maddon et al. 1985]) was digested with EcoRI to produce the cDNA insert. This fragment was recovered by polyacrylamide gel electrophoresis (fragment 1).

pUC18 was digested with EcoRI and the single fragment recovered by polyacrylamide gel electrophoresis (fragment 2). Fragment 1 was ligated to fragment 2 and the ligation mixture transformed into E. coli strain 294. The transformed culture was plated on ampicillin media plates and resistant colonies selected. Plasmid DNA was prepared from transformants and checked by restriction analysis for the presence of the correct DNA fragments. This plasmid is referred to as pUCCD4.

pSVeE'DHFR (Muesing et al., Cell 48:691–701 [1987]) was digested with KpnI and BamHI and blunted with E. coli DNA polymerase I (Klenow fragment) and the four dNTPs. Fragment 3 containing the pML-$Amp^r$ region, SV40 early promoter, the HIV LTR, and the mouse DHFR gene was recovered by gel electrophoresis, ligated and the ligation mixture transformed into E. coli strain 294. The transformed culture was plated on ampicillin media plates and resistant colonies selected. Plasmid DNA was prepared from transformants and checked by restriction analysis for the presence of the BamHI restriction site and the absence of the KpnI restriction site. This plasmid is referred to as pSVeΔBKDHFR and allows EcoRI-BamHI fragments to be inserted after the SV40 early promoter and transcribed under its control, following transfection into an appropriate cell line.

Synthetic oligonucleotides (adaptors 1–8, below) were made to extend from 76 bp 5' of the initiation codon of CD4 translation to the RsaI restriction site at 121 bp 3' of the initiator, with the sequence AATT at the 5' end of the sense strand to generate an end which could ligate to an EcoRI restriction fragment. These oligonucleotides were ligated and the 204 bp fragment containing the entire sequence recovered by gel electrophoresis (fragment 4).

```
CD4 adaptor 1:
AATTCAAGCCCAGAGCCCTGCCATTTCTGTGGGCTCAGGTCCCT

CD4 adaptor 2:
pACTGCTCAGCCCCTTCCTCCCTCGGCAAGGCCACAATGAACCGGGGAGT
C

CD4 adaptor 3:
pCCTTTTAGGCACTTGCTTCTGGTGCTGCAACTGGCGCTCCTCCCAGC

CD4 adaptor 4:
pAGCCACTCAGGGAAACAAAGTGGTGGTGGGCAAAAAAGGGGATACAGTG
GAACTGACCTCT

CD4 adaptor 5:
pACAGGTCAGTTCCACTGTATCCCCTTTTTTGCCCAGCACCACTTTGTTT
CC

CD4 adaptor 6:
pCTGAGTGGCTGCTGGGAGGAGCGCCAGTTGCAGCACCAGAAGCAAGT

CD4 adaptor 7:
pGCCTAAAAGGGACTCCCCGGTTCATTGTGGCCTTGCCGAGGGAGGAAGG
G

CD4 adaptor 8:
GCTGAGCAGTAGGGACCTGAGCCCACAGAAATGGCAGGGCTCTGGCTTG
``` pUCCD4 was digested with RsaI and SstI and the 401 bp fragment containing part of the CD4 coding sequence recovered by gel electrophoresis (fragment 5). pUC18 was digested with EcoRI and SstI and the fragment comprising the bulk of the plasmid recovered by gel electrophoresis (fragment 6). Fragments 4 and 5 were ligated to fragment 6 and the ligation mixture transformed into E. coli strain 294. The transformed culture was plated on ampicillin media plates and resistant colonies selected. Plasmid DNA was prepared from transformants and checked by restriction analysis for the presence of the correct fragment. The sequence of the inserted synthetic DNA was checked by excising the 605 bp EcoRI-SstI fragments from several transformants and ligating them to M13 mp19 which had been digested with the same enzymes. After transformation into E. coli strain JM101, single-stranded DNA was prepared and sequenced. One plasmid which contained the correct sequence was selected, and is referred to as pCD4int.

pCD4int was digested with EcoRI and SstI and fragment 7 containing the 5' end of the CD4 coding region was recovered by gel electrophoresis. pUCCD4 was digested with SstI and BamHI and the 1139 bp fragment containing the remainder of the CD4 coding region (fragment 8) recovered by gel electrophoresis.

pSVeΔBKDHFR was digested with EcoRI and BamHI and fragment 9 comprising the bulk of the plasmid was isolated. Fragments 7, 8 and 9 were ligated and the ligation mixture transformed into E. coli strain 294. The transformed culture was plated on ampicillin media plates and the resistant colonies selected. Plasmid DNA was prepared from transformants and checked by restriction analysis for the presence of the correct fragment. This plasmid is referred to as pSVeCD4DHFR, and was used to direct synthesis of recombinant intact CD4.

Section 2

A plasmid was constructed to direct the synthesis of a CD4 derivative lacking the putative transmembrane domain and most of the putative cytoplasmic domain (Maddon et al.). This was done with the intention of creating a secreted form of CD4, based on the assumption that these domains anchor the CD4 glycoprotein to the cell membrane, and that their deletion would result in the secretion of the product. This plasmid is referred to as pSVeCD4ΔNlaDHFR and was constructed as follows:

pUCCD4 was digested with SstI and TaqI and the 531 bp fragment (fragment 10) recovered. pUCCD4 was digested with NlaIII and TaqI and the 112 bp fragment (fragment 11) recovered. pUCCD4 was digested with BamHI and NlaIII and the 301 bp fragment (fragment 12) recovered. pCD4int was digested with SstI and BamHI and fragment 13 comprising the bulk of the plasmid recovered. Fragments 10, 11, and 12 were ligated together with fragment 13 and the ligation mixture transformed into E. coli strain 294. The transformed culture was plated on ampicillin media plates and resistant colonies selected. Plasmid DNA was prepared from transformants and checked by restriction analysis for the presence of the correct fragment. Plasmid DNA from several transformants was sequenced to ensure that the 195 bp NlaIII fragment had been deleted and that the proper reading frame was restored. The resulting plasmid is referred to as pCD4ΔNla.

pCD4ΔNla was digested with EcoRI and BamHI and the 1541 bp fragment containing the sequence of a CD4 derivative lacking the transmembrane and cytoplasmic domains recovered (fragment 14) and ligated to fragment 9 and the ligation mixture transformed into E. coli strain 294. The transformed culture was plated on ampicillin media plates and resistant colonies selected. Plasmid DNA was prepared from transformants and checked by restriction analysis for the presence of the correct fragment. This plasmid is referred to as pSVeCD4ΔNlaDHFR.

Both pSVeCD4DHFR and pSVeCD4ΔNlaDHFR were transfected into CHO cells by the same method used to establish cell lines stably expressing HIV-I polypeptides (Muesing, Smith and Capon, Cell 48:6910701 [1987]). These cells were assayed for production by radioimmunoprecipitation as described below. While no product was detected in initial experiments, subsequent experiments showed that the above described coding segment could indeed direct the synthesis of a soluble CD4 adheson variant both in CHO and 293 cells.

Section 3

A different expression system was initially used for the synthesis and expression of a CD4 variant lacking completely the cytoplasmic and transmembrane domains. This system uses the cytomegalovirus promoter and can be used in cultured cells of human origin. The first plasmid constructed for use in this system contained the entire coding region for CD4 and was intended to function as a control in the following studies. It is referred to as pRKCD4, and was constructed as follows:

pSVeCD4DHFR was digested with EcoRI and BamHI and fragment 15 containing the entire CD4 coding region was isolated. pRK5 (U.S. Ser. No. 97,472, filed Sep. 11, 1987) was digested with EcoRI and BamHI and fragment 16 comprising the bulk of the plasmid recovered by gel electrophoresis, ligated to fragment 15, and the ligation mixture transformed into E. coli strain 294. The transformed culture was plated on ampicillin media plates and resistant colonies selected. Plasmid DNA was prepared from transformants and checked by restriction analysis for the presence of the correct fragment. This plasmid is referred to as pRKCD4.

Section 4

The next plasmid constructed was designed to direct the expression of the above-mentioned (Section 3) secreted derivative of CD4. The coding region of CD4 was fused after amino acid residue 368 of mature CD4 to a sequence from pBR322 which codes for 9 more residues before a translation termination codon. This removes the putative CD4 transmembrane and cytoplasmic domains, which are presumed to anchor CD4 to the cell surface. The plasmid is referred to as pRKCD4T (and which produces protein called CD4T), and was constructed as follows:

pSVeCD4DHFR was digested with HpaII, blunted with Klenow fragment and the four dNTPs, and digested with BstEII. The 382 bp fragment (fragment 17) containing part of the CD4 coding sequence was recovered by gel electrophoresis. pSVeCD4DHFR was digested with EcoRI and BstEII and the 874 bp fragment (fragment 18) recovered. pBR322 was digested with HindIII, blunted with Klenow fragment and the four dNTPs, and digested with EcoRI. Fragment 19 comprising the bulk of the plasmid was isolated and ligated to fragments 17 and 18 and the ligation mixture transformed into E. coli strain 294. The transformed culture was plated on ampicillin media plates and resistant colonies selected. Plasmid DNA was prepared from transformants and checked by restriction analysis for the presence of the correct fragment. This plasmid is referred to as pCD4Tint.

pRK5 was digested with EcoRI and SmaI and fragment 20 comprising the bulk of the plasmid isolated. pCD4Tint was digested with EcoRI and EcoRV and the 1410 bp fragment containing the CD4 coding sequence to the HpaII site at 1176 bp 3' of the initiating codon and the 154 bp HindIII-EcoRV fragment of pBR322 was recovered (fragment 21). Fragments 20 and 21 were ligated and the ligation mixture transformed into E. coli strain 294. The transformed culture was plated on ampicillin media plates and resistant colonies selected. Plasmid DNA was prepared from transformants and checked by restriction analysis for the presence of the correct fragment. This plasmid is referred to as pRKCD4T.

Section 5a

In order to create a secreted form of CD4 which could be purified with an antibody directed to herpes virus type I glycoprotein D, a plasmid was constructed to express a derivative of CD4T in which the region coding for the mature, processed CD4T polypeptide was fused to a sequence coding for the signal peptide and the first 27 residues of the mature type I Herpes Simplex Virus gD glycoprotein. This plasmid is referred to as pRKGDCD4T, and was constructed as follows:

pgDTrunc.DHFR was digested with EcoRI and PvuII and the fragment containing the coding region for the signal peptide and first 27 residues of the mature HSV I gD glycoprotein was isolated (fragment 22). pRKCD4T was digested with EcoRI and BstEII and fragment 23 containing the 3' end of the CD4 coding sequence and the pRK5 region was isolated.

Synthetic oligonucleotides GD (adaptors 1–2, below) containing the coding sequence of CD4 from the codon for the amino terminal residue of mature CD4 to the RsaI site at 121 bp 3' of translation initiation, and containing the sequence CTGCTCGAG at the 5' end of the sense strand were prepared (fragment 24). pRKCD4 was digested with RsaI and BstEII and the 665 bp fragment containing part of the coding region for CD4 was recovered (fragment 25) and ligated to fragment 24. After digestion with BstEII to ensure that only monomeric fragment was present, the 724 bp fragment containing both sequences was recovered by gel electrophoresis (fragment 26).

Fragments 22, 23 and 26 were ligated and the ligation mixture transformed into E. coli strain 294. The transformed culture was plated on ampicillin media plates and resistant colonies selected. Plasmid DNA was prepared from transformants and checked by restriction analysis for the presence of the correct fragment. The sequence of several transformants was checked to ensure that the synthetic insert was correct and that reading frame was preserved. This plasmid is referred to as pRKGDCD4T.

These pRK5 derived plasmids preferably were transfected into 293S cells for stable expression according to Muesing, et al. Cell 48:691 (1987) with the exception that in addition to the plasmid of interest a plasmid expressing the neomycin resistance gene pRSV neo (Gorman et al. Science 221:553–555 (1985)) was cotransfected. 293 cells also are used satisfactorily as host cells. 2 days after transfection, the cells were passaged into standard medium (1:1 F12/DME supplemented with L-glutamine, penicillin-streptomycin and 10% FBS) with 0.5 mg/ml G418 (Genticin sulfate; Gibco) for selection of stable cell lines, rather than in media containing methotrexate as shown by Muesing et al. Cells were assayed for production of CD4 or CD4 analogs by radioimmunoprecipitation. Binding studies (section 5c) used conditioned supernatants from these cells in the 1:1 F12/DME medium. Materials used in infectivity assays (section 5b) were obtained as described in section 8 below.

```
gDCD4 adaptor 1:
CTGCTCGAGCAGGGAAACAAAGTGGTGCTGGGCAAAAAGGGGATACAGTG
                                         GAACTGAC gDCD4 adaptor 2:
pACAGGTCAGTTCCACTGTATCCCCTTTTTTGCCCAGCACCACTTTGTTT
                                         CCCTGCTCGA
```

Section 5b

The following constitutes a study of the neutralization of HIV-1 infectivity by soluble CD4 analogs. A modification of the neutralization procedure of Robert-Guroff et al., Nature 316:72 (1985) was followed. Equal volumes of inhibitor supernatant and virus (60 microliters) were incubated at 4 degrees C. for 1 hour, then the same volume of H9 (Gallo et al., Science 224:500, 1984) at $5 \times 10^6$/ml was added and incubation continued for 1 hour at 37 degrees C. Following absorption, $2.5 \times 10^5$ cells in 150 microliters were transferred to 2 ml of incubation media. After 4 days at 37 degrees C., the cultures were split 1:2 with fresh media and incubated for an additional 3 days. Cultures were harvested, reverse transcriptase activity was measured (Groopman et al., AIDS Research and Human Retroviruses 3:71, 1987), and immunofluorescence reactivity with HIV-1 positive serum was determined as described (Poiesz et al., Proc. Acad. Nat. Sci. USA 77:7415, 1980). Inhibitor supernatants were obtained from confluent plate cultures of 293S/CDT4, 293S/gDCD4T cells or untransfected 293S cells by replacing the growth medium incubation media and harvesting the supernatants 24 hours later. Inhibitor supernatant replaced part or all of the incubation media during the first three days of culture as indicated in the second column of Table 3. Challenge dose of virus was 100 $TCID_{50}$ (Groopman et al., supra) of HIV-1 strain HTLV-IIIB grown in H9 cells assayed in the same system. Incubation media consisted of RPMI 1640 media containing 2 mM L-glutamine, 100 units/ml penicillin, 100 micrograms/ml streptomycin, 2 micrograms/ml polybrene and 20% fetal calf serum (M.A. Bioproducts).

TABLE 3

| Inhibitor supernatant | Dilution of Inhibitor supernatant | Indirect immunofluorescence (% positive cells) | | Reverse transcriptase (cpm/ml × 10⁵) | |
|---|---|---|---|---|---|
| mock-trans-fected | undil.; 1:4 | 65.3 | 65.5 | 21.8 | 23.9 |
| mock-trans-fected | undil.; 1:4 | 61.2 | 61.1 | 18.5 | 28.1 |
| CD4T | undil.; 1:4 | 0.4 | 18.0 | 0.11 | 5.94 |
| CD4T | undil.; 1:4 | 0.8 | 16.1 | 0.15 | 3.72 |
| gDCD4T | undil.; 1:4 | 0.4 | 26.8 | 0.14 | 9.92 |
| gDCD4T | undil.; 1:4 | 1.4 | 36.1 | 0.23 | 11.3 |

Both forms of soluble CD4 virtually abolished the growth of HIV-1, when incubated with virus-infected cells without prior dilution (Table 2). At a dilution of 1:4 the soluble CD4 preparations were only partially effective in inhibiting virus growth, however the level of fluorescent-positive cells and reverse transcriptase was still significantly lower than cultures receiving mock-transfected cell supernatants (Table 2). Since there was no significant difference in virus growth between diluted and undiluted control supernatants, nor did any of the supernatants affect the growth of uninfected H9 cells (data not shown), soluble CD4 proteins present in these supernatants were concluded to be responsible for the neutralization of HIV-1 infection of H9 cells.

Section 5c

To determine the affinity constant for interactions between gp120 and CD4 or CD4 variants, saturation binding analysis was carried out with soluble CD4 (supra) and detergent solubilized intact CD4 (Lasky et al. Cell 50:975 [1987]) employing radioiodinated gp120 labeled with lactoperoxidase. Binding reactions consisted of $^{125}$I-gp120 (3 ng to 670 ng, 2.9 nCi/ng) incubated for 1 hour at 0 degrees C. with cell lysates containing intact CD4 (Laskey et al., op cit.) or cell supernatants containing unlabeled CD4T or gDCD4T prepared as described in section 5a. Reactions (0.2 ml) had a final composition of 0.5× McDougal Lysis Buffer (McDLB) (1× McDLB contains 0.5% Nonidet NP-40, 0.2% Na deoxycholate, 0.12 M NaCl, 0.02 M Tris-HCl, pH 8.0) and were performed in duplicate, both in the presence or absence of 50 micrograms of unlabeled purified gp120 (74 fold or greater excess). Following incubation, bound gp120 was quantitated by immunoprecipitation and counted in a gamma counter. For immunoprecipitation, binding reaction solutions were preabsorbed with 5 microliters of normal rabbit serum for one hour at 0° C., and cleared with 40 microliters of Pansorbin (10% w/v, Calbiochem) for 30 minutes at 0 degrees C. Samples were then incubated overnight at 0 degrees C. with 2 microliters of normal serum or 5 microliters (0.25 microgram) of OKT4 monoclonal antibody (Ortho) followed by collection of immune complexes with 10 microliters of Pansorbin. Precipitates were washed twice in 1× McDLB and once in water, then eluted by eluting at 100 degrees C. for 2 minutes in sample buffer (0.12 M Tris-HCl pH 6.8, 4% SDS, 0.7 M mercaptoethanol, 20% glycerol, and 0.1% bromophenol blue). CD4 molecules were bound saturably by gp120, and yielded a simple mass action binding curve. Supernatants from mock-transfected cells gave a level of specifically bound gp120 less than 1% that found for supernatants containing soluble CD4. Scatchard analysis revealed a single class of binding sites on each molecule, with apparent dissociation constants (Kd) of $1.3 \times 10^{-9}$ M, $0.83 \times 10^{-9}$ M and $0.72 \times 10^{-9}$ M for intact CD4, CD4T and gDCD4T, respectively. The values obtained for CD4-gp120 binding in solution are comparable to the affinity previously measured for gp120 binding to CD4 on whole cells (Kd-$4.0 \times 10^{-9}$ M. Lasky, Cell, supra).

Section 6

In order to produce secreted derivatives of CD4 which are free of extraneous amino acid residues, two plasmids were constructed for expression in 293 cells. The plasmids contain CD4 genes which have been truncated without the addition of extra residues, and are referred to as pRKCD4ΔNla and pRKCD4TP (and which produce proteins called CD4TP and CD4ΔNla), and were constructed as follows:

Fragment 14 containing the CD4 gene with the 195 bp NlaIII restriction fragment deleted was ligated to fragment 16, which is pRK5 digested with EcoRI and BamHI. The ligation mixture was transformed into E. coli strain 294, the transformed culture plated on ampicillin media plates and resistant colonies selected. Plasmid DNA was prepared from transformants and checked by restriction analysis for the presence of the correct fragment. The resulting plasmid is referred to as pRKCD4ΔNla.

Synthetic DNA (5' CGT GAT AGA AGC TTT CTA GAG 3') was made to attach to the HpaII site at 1176 bp and which when so attached would terminate translation after amino acid residue 368 of mature CD4 (fragment 27). The other end of this fragment was designed to ligate to BamHI restriction fragments. pUCCD4 was digested with BstEII and HpaII and the 382 bp fragment containing part of the CD4 gene was recovered (fragment 28). Fragments 27 and 28 were ligated and then digested with BstEII to reduce dimerized fragments to monomers, and the resulting 401 bp fragment was recovered (fragment 29).

pRKCD4 was digested with BstII and BamHI and the fragment comprising the bulk of the plasmid (fragment 30) was isolated and ligated to fragment 29. The ligation mixture was transformed into E. coli strain 294, the transformed culture plated on ampicillin media plates and resistant colonies selected. Plasmid DNA was prepared from transformants and checked by restriction analysis for the presence of the correct fragment. The resulting plasmid is referred to as pRKCD4TP. Both plasmids are transfected into 293 cells to generate stable variant CD4-expressing cell lines as described above.

Section 7

Two plasmids were constructed to direct the expression of secreted CD4 lacking extraneous amino acid residues in CHO cells. These are referred to as pSVeCD4ΔNlaSVDHFR and pSVeCD4TPSVDHFR (and which encode proteins having the primary sequence of CD4ΔNla and CD4TP), and were constructed as follows:

pE348HBV.E400D22 was digested with PvuI and EcoRI and the fragment containing the SV40 early promoter and part of the β-lactamase gene was recovered (fragment 31). pE348HBV.E400D22 was digested with PvuI and BamHI and the large fragment containing the balance of the β-lactamase gene as well as the SV40 early promoter and the DHFR gene was isolated (fragment 32).

Fragments 31 and 32 were ligated together with fragment 14 and transformed into E. coli strain 294. The transformed culture was plated on ampicillin media plates and resistant colonies selected. Plasmid DNA was prepared from transformants and checked by restriction analysis for the presence of the correct fragment. The resulting plasmid is referred to as pSVECD4ΔNlaSVDHFR. This plasmid contains the same DNA fragment encoding the soluble CD4 molecule found in the above-mentioned plasmid pSVeCD4ΔNlaDHFR (Section 2).

pRKCD4TP was digested with EcoRI and BamHI and the fragment containing the truncated CD4 coding region was isolated and ligated to fragments 31 and 32. The ligation mixture was transformed into *E. coli* strain 294, the transformed culture plated on ampicillin media plates and resistant colonies selected. Plasmid DNA was prepared from transformants and checked by restriction analysis for the presence of the correct fragment. The resulting plasmid is referred to as pSVeCD4TPSVDHFR. Both of these plasmids are transfected into CHO cells and amplified transfectants selected by methotrexate using conventional procedures.

EXAMPLE 2

Fusions of the V region of the CD4 gene, which is homologous to the variable region of immunoglobulin genes (ref Maddon et al. 1985), to the constant (C) region of human immunoglobulin κ and γ2 chains are constructed as follows:

Synthetic DNA is made to code for the C region of human κ chain (residues 109–214) based on the sequence published by Morin et al., Proc. Natl. Acad. Sci. 82:7025–7029, with the addition at the 5' end of the coding strand of the sequence GGGG, which allows this fragment to be ligated to the BspMI site at the end of the putative V-like region of CD4. At the 3' end of the coding region, a translational stop codon is added as well as a sequence which allows this end to be ligated to BamHI restriction fragments. The synthetic DNA is made in 8 fragments, 4 for each strand, 70–90 bases long. These are then allowed to anneal and ligated prior to isolation on a polyacrylamide gel (fragment 33).

pRKCD4 is digested with EcoRI and BspMI and the 478 bp fragment containing the region coding for the putative V-like domain of CD4 is recovered (fragment 34). Fragments 33 and 34 are ligated together with fragment 16 (from the expression vector pRK5). The ligation mixture is transformed into *E. coli* strain 294, the transformed culture plated on ampicillin media plates and resistant colonies selected. Plasmid DNA is prepared from transformants and checked by restriction analysis for the presence of the correct fragment. The resulting plasmid is referred to as pRKCD4Ck.

A plasmid encoding a fusion of the CD4 V-like domain to the human immunoglobulin Cγ2 region is constructed in a similar fashion, and is referred to as pRKCD4Cγ2. Both of these plasmids are transfected into 293 cells, myeloma cells or other competent cells in order to obtain cell lines expressing variant CD4 molecules as described above.

EXAMPLE 3

The gDCD4T secreted by the method of Example 1 was purified from cell culture fluid containing either 10% FBS (fetal bovine serum) or no added FBS. The conditioned cell culture fluid was first concentrated by ultrafiltration then purified by immunoaffinity chromatography. The immunoaffinity column was produced by coupling murine monoclonal antibody 5B6 (whose epitope is on the HSV-1 gD portion of the gDCD4T molecule) to glyceryl coated controlled pore glass by the method of Roy et al., 1984. The concentrated cell culture fluid is applied directly to the column and the contaminating proteins are washed away with neutral pH buffer. The column is then washed with neutral buffer containing tetramethylammonium chloride followed by neutral buffer containing Tween 80. The bound gDCD4T is eluted from the column with buffer at pH 3 containing Tween 80 (0.1% w/v) and is neutralized immediately as it is eluted. The eluted neutralized gDCD4T is then concentrated by ultrafiltration and dialyzed/diafiltered to exchange the buffer for a physiological salt solution containing Tween 80 at approximately 0.1% w/v.

If the detergent is not present the gDCD4T forms aggregates as evidenced by the ability of centrifugation at approximately 10,000× g for 2 minutes to remove the gDCD4T from the solution. Incubation of gDCD4T at 4° C. in 0.1M sodium acetate, 0.5M NaCl and 0.25M tris at pH 7 together with BSA, Tween 80 or glycerol as candidate stabilizers showed that, in the absence of a stabilizer the gDCD4T gradually aggregated over the space of 12 days to the point where only about 60–70% of the protein was soluble. However, use of 0.1% w/v Tween 80 or (0.5 mg/ml BSA ensured that about 100% or 80%, respectively, of the gDCD4T remained soluble over this period. Surprisingly glycerol was ineffective as a stabilizer and produced results inferior even to the control—at 8 days about 80% of the gDCD4T was aggregated when stored in the presence of glycerol.

EXAMPLE 4

Plasmids were constructed to direct the expression of proteins containing differing lengths of the amino-terminal, extracellular domain of CD4 fused to the constant region of human immunoglobulin γ1. These plasmids are referred to as pRKCD4$_{2\gamma1}$, pRKCD4$_{e4\gamma1}$, pRKCD4$_{2\gamma1}$, pRKCD4$_{e2\gamma1}$, pRKCD4$_{1\gamma1}$, and pRKCD4$_{e1\gamma1}$.

Plasmid pRKCD4$_{4\gamma1}$ contains the portion of the CD4 gene from the initiation codon to the fusion site after the codon for serine reside 366 of the mature CD4 polypeptide, immediately followed by the sequence coding for the constant region of human immunoglobulin γ1, starting at the codon for serine residue 114 of mature human immunoglobulin γ1 (Kabat et al.).

Plasmid pRKCD4$_{e4\gamma1}$ contains the portion of the CD4 gene from the initiation codon to the fusion site after the codon for lysine residue 360 of the mature CD4 polypeptide, immediately followed by the sequence coding for the constant region of human immunoglobulin γ1, starting at the codon for serine residue 114 of mature human immunoglobulin γ1 (Kabat et al.).

Plasmid pRKCD4$_{2\gamma1}$ contains the portion of the CD4 gene from the initiation codon to the fusion site after the codon for glutamine residue 180 of the mature CD4 polypeptide, immediately followed by the sequence coding for the constant region of human immunoglobulin γ1, starting at the codon for serine residue 114 of mature human immunoglobulin γ1 (Kabat et al.).

Plasmid pRKCD4$_{e2\gamma1}$ contains the portion of the CD4 gene from the initiation codon to the fusion site after the codon for leucine residue 177 of the mature CD4 polypeptide, immediately followed by the sequence coding for the constant region of human immunoglobulin γ1, starting at the codon for serine residue 114 of mature human immunoglobulin γ1 (Kabat et al.).

Plasmid pRKCD4$_{1\gamma1}$ contains the portion of the CD4 gene from the initiation codon to the fusion site after the codon for aspartic acid residue 105 of the mature CD4 polypeptide, immediately followed by the sequence coding for the constant region of human immunoglobulin γ1, starting at the codon for serine residue 114 of mature human immunoglobulin γ1 (Kabat et al.).

Plasmid pRKCD4$_{e1\gamma1}$ contains the portion of the CD4 gene from the initiation codon to the fusion site after the codon for leucine residue 100 of the mature CD4 polypeptide, immediately followed by the sequence coding for the constant region of human immunoglobulin γ1, starting at the codon for serine residue 114 of mature human immunoglobulin γ1 (Kabat et al.).

Construction of these plasmids required the prior construction of plasmid pRKCD4TP/γ1. It was constructed as follows:

A cDNA clone coding for human immunoglobulin γ1 was obtained from a human spleen cDNA library (Clontech Laboratories, Inc.) using oligonucleotides based on the published sequence (Ellison et al., "Nucl. Acids Res." 10:4071–4079 [1982]), and an EcoRI-EagI fragment (the EcoRI site was contributed by a linker; see FIGS. 4a, b) containing part of the variable and all of the constant region was obtained. This fragment was blunted with Klenow fragment, and recovered by gel electrophoresis (Fragment a1).

Plasmid pRKCD4TP-kk, encoding a substitutional variant of soluble CD4 (residues 1–368) containing a lysine residue instead of asparagine at position 1 of the mature polypeptide, was constructed from plasmid pRKCD4TP by site-directed mutagenesis. A synthetic oligonucleotide was made as a primer for a mutagenesis reaction to obtain the desired coding sequence. This was synthesized as a 51-mer which contained two silent mutations from the natural sequence in addition to the substitution mutation, and 21 bases on each side of the mutated codons:

```
5'-CCC TTT TTT GCC CAG CAC CAC CTT CTT GCC CTG-
AGT GGC TGC TGG GAG GAG-3'
```

Plasmid pRKCD4TP was transformed into E. coli strain SR101 and the transformed colonies plated on ampicillin media plates. Resistant colonies were selected and grown in the presence of m13K07 helper bacteriophage to yield secreted, encapsidated single-stranded templates of pRKCD4TP. The single-stranded plasmid DNA was isolated and used as the template for mutagenesis reactions with the synthetic oligonucleotides described above as primers. The mutagenesis reaction was transformed E. coli SR101 and the transformed culture plated on ampicillin media plates. Transformants were screened by colony hybridization (ref. Grunstein-Hogness) for the presence of the appropriate sequence, using the following 16 mer as the probe.

5'-C CAC CTT CTT GCC CTG-3'

The hybridization conditions chosen were sufficiently stringent that the probe only detects the correctly fused product. Colonies identified as positive were selected and plasmid DNA was isolated and transformed into E. coli strain SR101. The transformed cultures were plated on ampicillin media plates, and resistant colonies were selected and grown in the presence of m13K07 bacteriophage. Templates were prepared as above and screened by sequencing.

Plasmid pRKCD4TP-kk was digested with XbaI and treated with Klenow Enzyme, and Fragment a2, containing the linearized plasmid was recovered by gel electrophoresis, and ligated with fragment a1. The ligation mixture was transformed into E. coli strain 294, the transformed culture plated on ampicillin media plates and resistant colonies selected. Plasmid DNA was prepared from the transformants and checked by restriction analysis for the presence of the correct fragment in the correct orientation (i.e., the immunoglobulin coding region in the same orientation as the CD4 coding region, and at the 3' end of the CD4 coding region). This plasmid is referred to as pRKCD4TP/γ1.

Synthetic oligonucleotides were made as primers for deletional mutagenesis reactions to fuse the appropriate coding sequences of IgG1 and CD4 as described above. These were synthesized as 48-mers comprising 24 nucleotides on each side of the desired fusion site (i.e., corresponding to the COOH-terminal 8 residues of the desired CD4 moiety, and the $NH_2$-terminal 8 residues of the desired immunoglobulin moiety). Plasmid pRKCD4TP/γ1 was transformed into E. coli strain SR101 and the transformed cultures plated on ampicillin media plates. Resistant colonies were selected and grown in the presence of m13K07 helper bacteriophage to yield secreted, encapsidated single-stranded templates of pRKCD4TP/γ1. The single-stranded plasmid DNA was isolated and used as the template for mutagenesis reactions with the synthetic oligonucleotides described above as primers. The mutagenesis reactions were transformed E. coli SR101 and the transformed culture plated on ampicillin media plates. Transformants were screened by colony hybridization (ref. Grunstein-Hogness) for the presence of the appropriate fusion site, using 16mers as probes. These 16mers comprise 8 bases on either side of the fusion site, and the hybridization conditions chosen were sufficiently stringent that the probes only detect the correctly fused product. Colonies identified as positive were selected and plasmid DNA was isolated and transformed into E. coli strain SR101. The transformed cultures were plated on ampicillin media plates, and resistant colonies were selected and grown in the presence of m13K07 bacteriophage. Templates were prepared as above and screened by sequencing.

The plasmids were transfected into 293 cells using standard procedures and assayed for expression and production as described above.

|  | Expressed | Secreted |
|---|---|---|
| $pRKCD4_{1\gamma1}$ | + | − |
| $pRKCD4_{e2\gamma1}$ | + | + |
| $pRKCD4_{2\gamma1}$ | + | + |
| $pRKCD4_{e4\gamma1}$ | + | + |
| $pRKCD4_{4\gamma1}$ | + | + |

Plasmids also were constructed to direct the expression of fusion proteins containing differing lengths of the amino-terminal, extracellular domain of CD4 fused to the truncated portion of the constant region of human immunoglobulin γ1, comprising only the hinge region and constant domains $CH_2$ and $CH_3$.

Synthetic oligonucleotides were made as primers for mutagenesis reactions to delete the immunoglobulin sequence from Ser114 to Cys215 inclusive (Kabat et al.). These were synthesized as 48-mers comprising 24 nucleotides on each side of the desired fusion site (i.e., corresponding to the COOH-terminal 8 residues of the desired CD4 moiety, and the $NH_2$-terminal 8 residues of the desired immunoglobulin moiety). Plasmids $pRKCD4_{4\gamma1}$, $pRKCD4_{2\gamma1}$ and $pRKCD4_{1\gamma1}$ were separately transformed into E. coli strain SR101 and the transformed culture plated on ampicillin media plates. Resistant colonies were selected and grown in the presence of m13K07 helper bacteriophage to yield secreted, encapsidated single-stranded templates of these plasmids. The single-stranded plasmid DNA was isolated and used as the template for mutagenesis reactions with the synthetic oligonucleotides described above as primers. The mutagenesis reactions were transformed E. coli SR101 and the transformed culture plated on ampicillin media plates. Transformants were screened by colony hybridization (Grunstein-Hogness) for the presence of the appropriate fusion site, using 16mers as probes. These 16mers comprise 8 bases on either side of the fusion site, and the hybridization conditions chosen were sufficiently stringent that the probes only detect the correctly fused product. Colonies identified as positive were selected and plasmid DNA was isolated and transformed into E. coli strain SR101. The transformed cultures were plated on ampicillin media plates, and resistant colonies were selected and grown in the presence of m13K07 bacteriophage. Templates were prepared as above and screened by sequencing.

The plasmid derived from plasmid pRKCD4$_{4\gamma1}$ is referred to as pRKCD4$_{4Fc1}$, that derived from plasmid pRKCD4$_{2\gamma1}$ is referred to as pRKCD4$_{2Fc1}$ and that derived from plasmid pRKCD4$_{1\gamma1}$ is referred to as pRKCD4$_{1Fc1}$.

pRKCD4$_{2Fc1}$, pRKCD4$_{1Fc1}$ and pRKCD4$_{4Fc1}$ are cultured in the same fashion as described above and CH1-deleted CD4 immunoadhesons recovered as described elsewhere herein.

Light Chain Fusions

Plasmids were constructed to direct the expression of proteins containing differing lengths of the amino terminal, extracellular domain of CD4 fused to the constant region of human immunoglobulin κ. These plasmids are referred to as pRKCD4$_{4\kappa}$, and pRKCD4$_{e4\kappa}$.

Plasmid pRKCD4$_{4\kappa}$ contains the portion of the CD4 gene from the initiation codon to the fusion site after the codon for serine residue 366 of the mature CD4 polypeptide, immediately followed by the sequence for the constant region of human immunoglobulin κ, starting at the codon for threonine residue 109 of the mature human immunoglobulin κ. (Kabat et al.)

Plasmid pRKCD4$_{e4\kappa}$ contains the portion of the CD4 gene from the initiation codon to the fusion site after the codon for lysine residue 360 of the mature CD4 polypeptide, immediately followed by the sequence for the constant region of human immunoglobulin κ, starting at the codon for threonine residue 109 of the mature human immunoglobulin κ. (Kabat et al.)

These plasmids were constructed in a manner analogous to plasmids pRKCD4$_{4\gamma1}$ and pRKCD4$_{e4\gamma1}$ described above, with the following exception:

The human immunoglobulin κ coding sequence (FIG. 5) was obtained from a human spleen cDNA library (Clontech Laboratories, Inc.) using oligonucleotides based on the published sequence (Hieter, P. A. et al., Cell 22:197–207 [1980]) and an EcoRI-BspMI fragment containing part of the variable region and the entire constant region was obtained (see FIG. 5). This fragment was blunted with Klenow fragment and the four dNTPs. This fragment was used instead of fragment a1, and was used to construct plasmid pRKCD4TP/hκ.

Expression in CHO Cells

Plasmids were or are constructed to direct the expression of the immunoadhesons described above in CHO cells. These are referred to as pSVeCD4$_{4\gamma1}$SVDHFR, pSVeCD4$_{2\gamma1}$SVDHFR, pSVeCD4$_{1\gamma1}$SVDHFR, pSVeCD4$_{e4\gamma1}$SVDHFR, pSVeCD4$_{e2\gamma1}$SVDHFR, pSVeCD4$_{e1\gamma1}$SVDHFR, pSVeCD4$_{4Fc1}$SVDHFR, pSVeCD4$_{2Fc1}$SVDHFR, pSVeCD4$_{1Fc1}$SVDHFR, pSVeCD4$_{4\kappa}$SVDHFR and pSVeCD4$_{2\kappa}$SVDHFR.

Fragment 31 was prepared as described above. Fragment 32a was prepared by digesting plasmid pE348HBV.E400 D22 with BamHI, blunting with Klenow fragment and the four dNTPs, then digesting with PvuI and isolating the large fragment containing the balance of the β-lactamase gene and the SV40 early promoter and the DHFR gene. Plasmids pRKCD4$_{4\gamma1}$, pRKCD4$_{2\gamma1}$, pRKCD4$_{1\gamma1}$, pRKCD4$_{e4\gamma1}$, pRKCD4$_{e2\gamma1}$, pRKCD4$_{e1\gamma1}$, pRKCD4$_{4Fc1}$, pRKCD4$_{2Fc1}$, pRKCD4$_{1Fc1}$, pRKCD4$_{4\kappa}$ and pRKCD4$_{2\kappa}$ were separately digested with HindIII, blunted with Klenow fragment and the four dNTPs, then digested with EcoRI and the fragments encoding the CD4-Ig fusion protein were isolated. The resulting DNA fragments were ligated together with fragments 31 and 32a and transformed into *E. coli* strain 294. Colonies were selected and checked for the presence of the correct plasmid as above, then transfected into CHO cells and amplified by methotrexate selection using conventional procedures.

EXAMPLE 5

Culture, Purification and Formulation of CD4 Variants

Plasmids encoding soluble CD4 adhesons such as CD4T, CD4TP, or soluble CD4 immunoadhesons were calcium phosphate transfected into CHO-DP7 (a proinsulin-transformed autocrine host cell derived from CHO; U.S. Ser. No. 97,472) and the transformants grown in selective medium (1:1 HAM F12/DMEM GHT$^-$ containing 1–10% diafiltered or dialyzed bovine serum). Other suitable host cells are CHO cells or 293S human embryonic kidney cells. The transformants were amplified by methotrexate selection in the same medium but containing 500 nm methotrexate. A subclone capable of secreting CD4TP, CD4tp 500 b, was selected. CD4tp 500 b is cultured in a DMEM/HAM F12 medium at about 37° C. until CD4TP accumulates in the culture, after which the medium is separated from the cells and insoluble matter by centrifuging.

Culture fluid from CD4TP transformants was concentrated and diafiltered to lower the ionic strength. The concentrate was passed through a large volume of Q-Sepharose anion exchange resin (previously equilibrated with 25 mM NaCl, pH 8.5) in order to adsorb contaminants from the culture fluid. The isoelectric point of CD4TP is about 9.5, thus making it possible to discriminate between truncated forms of CD4 and most contaminants by alternate adsorption, respectively, on a cation exchange resin such as carboxymethyl or sulfonyl Sepharose, and an anion exchange resin such as quaternary ammonium Sepharose. In addition, since highly electropositive domains are present in the extracellular segment of CD4 any CD4-containing variant is purified in the same fashion as CD4TP. The unadsorbed culture fluid from the anion exchange resin step was then passed through a cation exchange resin (previously equilibrated with 25 mM NaCl at pH 8.5) whereby CD4TP was adsorbed to the resin. The CD4TP was eluted with a NaCl gradient at pH 8.5, this CD4 variant eluting at about 0.2 M NaCl. Ammonium sulfate was added to the eluate to a concentration of 1.7M and the solution passed through a column of hydrophobic interaction chromatography resin (phenyl or butyl Sepharose). The CD4TP was eluted from the hydrophobic interaction column with a gradient of ammonium sulfate, the CD4TP emerging at about 0.7M ammonium sulfate. The eluate was concentrated and buffer exchanged on a G-25 column using phosphate buffered saline containing 0.02% (w/v) Tween 20 or Tween 80. The CD4TP was soluble and stable in this solution, which was sterile filtered and filled into vials as an aqueous formulation. Other polymeric nonionic surfactants are suitably used with the CD4 formulations, including Pluronic block copolymers or polyethylene glycol.

It is also possible to employ immunoaffinity purification of soluble CD4 wherein the CD4 is adsorbed onto an immobilized antibody against CD4. This method suffers from the disadvantage that elution of the soluble CD4 under acidic conditions leads to protein aggregation that is only thoroughly ameliorated at relatively higher levels of surfactant. The foregoing procedure permits the use of much lower quantities of surfactant, about from 0.01 to 0.10% (w/v) surfactant.

The procedure followed for the purification of CD4 fusions with immunoglobulin heavy chain was to concentrate recombinant supernatants by ultrafiltration and thereafter adsorb the fusion onto resin-immobilized Staphylococcal protein A. The fusion was eluted with 0.1M citrate buffer pH 3 with no salt or detergent. This preparation is buffered into Tris buffer at pH 7.5. The immunoglobulin fusions with CD4 V1–V4 optionally are further purified by the procedure described above for unfused CD4 variants. CD4 immunoglobulin fusions with CD4 V1–V2 also may be purified by the procedure above, except that it is not expected that the isoelectric point of this class of molecules will be as alkaline as that of species containing all four V regions of CD4.

EXAMPLE 6

The characteristics of several adheson variants were determined. As shown in table 4 the immunoadhesons $CD4_{4\gamma 1}$ and $CD4_{2\gamma 1}$ show improved plasma half-life in rabbits, coupled with high-affinity gp120 binding and an affinity for Fcγ receptor (determined with U937 cells) that is comparable to that of bulk human IgG1.

TABLE 4

|  | gp120 KD (nM)# | FcγR KD (nM)+ | Plasma Half-Life++ In Rabbits (Hrs.) |
|---|---|---|---|
| CD4T$ | 2.3 ± 0.4 | Not detected | 0.25 |
| $CD4_{4\gamma 1}$ | 1.2 ± 0.1 | 2.83 ± 0.25 | 6.4 |
| $CD4_{2\gamma 1}$ | 1.4 ± 0.1 | 3.01 ± 0.68 | 40.6 |
| human IgG1 | ND** | 3.52 ± 0.5 | 21 days* |

*determined in humans
+KD was determined by the method of Anderson et al., "J. Immunol." 125: 2735–2741 (1980).
determined by the method of Smith et al., "Science" 238: 1704–07 (1987).
$residues 1–368 only
++The adheson variant was injected intravenously into rabbits and samples of blood were collected periodically and assayed for the presence of the adheson variant.
**Not done.

What is claimed is:

1. A dimer of two polypeptides wherein each polypeptide of the dimer has the formula $AC_H$ wherein A is at least one immunoglobulin like domain of an adheson and $C_H$ is a constant region of an immunoglobulin heavy chain and A is fused at its C-terminus to the N-terminus of $C_H$.

2. The polypeptide dimer of claim 1 which is a homodimer.

3. The polypeptide dimer of claim 1 wherein A comprises more than one immunoglobulin-like domain(s) of the adheson.

4. The polypeptide dimer of claim 1 wherein A contains the ligand binding site of an adheson.

5. The polypeptide dimer of claim 1 wherein the constant region of the immunoglobulin is selected from constant regions of IgG, IgA, IgE, IgD and IgM.

6. The polypeptide dimer of claim 2 wherein the constant region of the immunoglobulin is selected from constant regions of IgG, IgA, IgE, IgD and IgM.

7. The polypeptide of claim 5 wherein the constant region of the immunoglobulin is the constant region of an IgG.

8. The polypeptide of claim 6 wherein the constant region of the immunoglobulin is the constant region of an IgG.

9. The polypeptide of claim 7 wherein the IgG is an IgG1 subtype.

10. The polypeptide of claim 8 wherein the IgG is an IgG1 subtype.

11. The polypeptide of claim 6 wherein A is at least one immunoglobulin like domain of an adheson selected from the group consisting of CD1, CD2, CD4, CD8, CD28, OX-2, I-CAM, N-CAM, LFA-3 and the high affinity IgE receptor.

12. The polypeptide of claim 8 wherein A is an immunoglobulin like domain of an adheson selected from the group consisting of CD1, CD2, CD4, CD8, CD28, OX-2, I-CAM, N-CAM, LFA-3 and the high affinity IgE receptor.

13. The polypeptide of claim 6 wherein the adheson is CD4.

14. The polypeptide of claim 8 wherein the adheson is CD4.

15. The polypeptide of claim 6 wherein the adheson is LFA-3.

16. The polypeptide of claim 8 wherein the adheson is LFA-3.

17. The polypeptide of claim 9 wherein the constant region of the IgG1 retains at least functionally active hinge, CH2 and CH3 domains.

18. The polypeptide of claim 17 wherein the adheson is CD4.

19. The polypeptide of claim 17 wherein the adheson is LFA-3.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 402 amino acids
      (B) TYPE: amino acid
      (D) TOPOLOGY: linear (xi) SEQUENCE DESCRIPTION: SEQ ID NO: 1:

```
Met Asn Arg Gly Val Pro Phe Arg His Leu Leu Leu Val Leu Gln
 1               5                  10                  15

Leu Ala Leu Leu Pro Ala Ala Thr Gln Gly Asn Lys Val Val Leu
                20                  25                  30

Gly Lys Lys Gly Asp Thr Val Glu Leu Thr Cys Thr Ala Ser Gln
                35                  40                  45

Lys Lys Ser Ile Gln Phe His Trp Lys Asn Ser Asn Gln Ile Lys
                50                  55                  60

Ile Leu Gly Asn Gln Gly Ser Phe Leu Thr Lys Gly Pro Ser Lys
                65                  70                  75

Leu Asn Asp Arg Ala Asp Ser Arg Arg Ser Leu Trp Asp Gln Gly
                80                  85                  90

Asn Phe Pro Leu Ile Ile Lys Asn Leu Lys Ile Glu Asp Ser Asp
                95                 100                 105

Thr Tyr Ile Cys Glu Val Glu Asp Gln Lys Glu Glu Val Gln Leu
               110                 115                 120

Leu Val Phe Gly Leu Thr Ala Asn Ser Asp Thr His Leu Leu Gln
               125                 130                 135

Gly Gln Ser Leu Thr Leu Thr Leu Glu Ser Pro Pro Gly Ser Ser
               140                 145                 150
```

```
Pro Ser Val Gln Cys Arg Ser Pro Arg Gly Lys Asn Ile Gln Gly
            155                 160                 165
Gly Lys Thr Leu Ser Val Ser Gln Leu Glu Leu Gln Asp Ser Gly
            170                 175                 180
Thr Trp Thr Cys Thr Val Leu Gln Asn Gln Lys Lys Val Glu Phe
            185                 190                 195
Lys Ile Asp Ile Val Val Leu Ala Phe Gln Lys Ala Ser Ser Ile
            200                 205                 210
Val Tyr Lys Lys Glu Gly Glu Gln Val Glu Phe Ser Phe Pro Leu
            215                 220                 225
Ala Phe Thr Val Glu Lys Leu Thr Gly Ser Gly Glu Leu Trp Trp
            230                 235                 240
Gln Ala Glu Arg Ala Ser Ser Ser Lys Ser Trp Ile Thr Phe Asp
            245                 250                 255
Leu Lys Asn Lys Glu Val Ser Val Lys Arg Val Thr Gln Asp Pro
            260                 265                 270
Lys Leu Gln Met Gly Lys Lys Leu Pro Leu His Leu Thr Leu Pro
            275                 280                 285
Gln Ala Leu Pro Gln Tyr Ala Gly Ser Gly Asn Leu Thr Leu Ala
            290                 295                 300
Leu Glu Ala Lys Thr Gly Lys Leu His Gln Glu Val Asn Leu Val
            305                 310                 315
Val Met Arg Ala Thr Gln Leu Gln Lys Asn Leu Thr Cys Glu Val
            320                 325                 330
Trp Gly Pro Thr Ser Pro Lys Leu Met Leu Ser Leu Lys Leu Glu
            335                 340                 345
Asn Lys Glu Ala Lys Val Ser Lys Arg Glu Lys Ala Val Trp Val
            350                 355                 360
Leu Asn Pro Glu Ala Gly Met Trp Gln Cys Leu Leu Ser Asp Ser
            365                 370                 375
Gly Gln Val Leu Leu Glu Ser Asn Ile Lys Val Leu Pro Thr Trp
            380                 385                 390
Ser Thr Pro Ser Phe Asn Ala Val Val Tyr His Ser
            395                 400         402

(2) INFORMATION FOR SEQ ID NO: 2:

(i) SEQUENCE CHARACTERISTICS:
        (A) LENGTH: 1416 bases
        (B) TYPE: nucleic acid
        (C) STRANDEDNESS: single
        (D) TOPOLOGY: linear (xi) SEQUENCE DESCRIPTION: SEQ ID NO: 2:

AATTCAAGCC CAGAGCCCTG CCATTTCTGT GGGCTCAGGT CCCTACTGCT              50

CAGCCCCTTC CTCCCTCGGC AAGGCCACAA TGAACCGGGG AGTCCCTTTT             100

AGGCACTTGC TTCTGGTGCT GCAACTGGCG CTCCTCCCAG CAGCCACTCA             150

GGGAAACAAA GTGGTGCTGG GCAAAAAAGG GGATACAGTG GAACTGACCT             200

GTACAGCTTC CCAGAAGAAG AGCATACAAT TCCACTGGAA AAACTCCAAC             250

CAGATAAAGA TTCTGGGAAA TCAGGGCTCC TTCTTAACTA AAGGTCCATC             300

CAAGCTGAAT GATCGCGCTG ACTCAAGAAG AAGCCTTTGG GACCAAGGAA             350

ACTTTCCCCT GATCATCAAG AATCTTAAGA TAGAAGACTC AGATACTTAC             400

ATCTGTGAAG TGGAGGACCA GAAGGAGGAG GTGCAATTGC TAGTGTTCGG             450
```

-continued

```
ATTGACTGCC AACTCTGACA CCCACCTGCT TCAGGGGCAG AGCCTGACCC       500

TGACCTTGGA GAGCCCCCCT GGTAGTAGCC CCTCAGTGCA ATGTAGGAGT       550

CCAAGGGGTA AAAACATACA GGGGGGGAAG ACCCTCTCCG TGTCTCAGCT       600

GGAGCTCCAG GATAGTGGCA CCTGGACATG CACTGTCTTG CAGAACCAGA       650

AGAAGGTGGA GTTCAAAATA GACATCGTGG TGCTAGCTTT CCAGAAGGCC       700

TCCAGCATAG TCTATAAGAA AGAGGGGGAA CAGGTGGAGT TCTCCTTCCC       750

ACTCGCCTTT ACAGTTGAAA AGCTGACGGG CAGTGGCGAG CTGTGGTGGC       800

AGGCGGAGAG GGCTTCCTCC TCCAAGTCTT GGATCACCTT TGACCTGAAG       850

AACAAGGAAG TGTCTGTAAA ACGGGTTACC CAGGACCCTA AGCTCCAGAT       900

GGGCAAGAAG CTCCCGCTCC ACCTCACCCT GCCCCAGGCC TTGCCTCAGT       950

ATGCTGGCTC TGGAAACCTC ACCCTGGCCC TTGAAGCGAA ACAGGAAAG       1000

TTGCATCAGG AAGTGAACCT GGTGGTGATG AGAGCCACTC AGCTCCAGAA      1050

AAATTTGACC TGTGAGGTGT GGGGACCCAC CTCCCCTAAG CTGATGCTGA      1100

GTTTGAAACT GGAGAACAAG GAGGCAAAGG TCTCGAAGCG GGAGAAGGCG      1150

GTGTGGGTGC TGAACCCTGA GGCGGGGATG TGGCAGTGTC TGCTGAGTGA      1200

CTCGGGACAG GTCCTGCTGG AATCCAACAT CAAGGTTCTG CCCACATGGT      1250

CCACCCCGAG CTTTAATGCG GTAGTTTATC ACAGTTAAAT TGCTAACGCA      1300

GTCAGGCACC GTGTATGAAA TCTAACAATG CGCTCATCGT CATCCTCGGC      1350

ACCGTCACCC TGGATGCTGT AGGCATAGGC TTGGTTATGC CGGTACTGCC      1400

GGGCCTCTTG CGGGAT                                          1416

(2) INFORMATION FOR SEQ ID NO: 3:

(i) SEQUENCE CHARACTERISTICS:
        (A) LENGTH: 1416 bases
        (B) TYPE: nucleic acid
        (C) STRANDEDNESS: single
        (D) TOPOLOGY: linear (xi) SEQUENCE DESCRIPTION: SEQ ID NO: 3:

TTAAGTTCGG GTCTCGGGAC GGTAAAGACA CCCGAGTCCA GGGATGACGA        50

GTCGGGGAAG GAGGGAGCCG TTCCGGTGTT ACTTGGCCCC TCAGGGAAAA       100

TCCGTGAACG AAGACCACGA CGTTGACCGC GAGGAGGGTC GTCGGTGAGT       150

CCCTTTGTTT CACCACGACC CGTTTTTTCC CCTATGTCAC CTTGACTGGA       200

CATGTCGAAG GGTCTTCTTC TCGTATGTTA AGGTGACCTT TTTGAGGTTG       250

GTCTATTTCT AAGACCCTTT AGTCCCGAGG AAGAATTGAT TTCCAGGTAG       300

GTTCGACTTA CTAGCGCGAC TGAGTTCTTC TTCGGAAACC CTGGTTCCTT       350

TGAAAGGGGA CTAGTAGTTC TTAGAATTCT ATCTTCTGAG TCTATGAATG       400

TAGACACTTC ACCTCCTGGT CTTCCTCCTC CACGTTAACG ATCACAAGCC       450

TAACTGACGG TTGAGACTGT GGGTGGACGA AGTCCCCGTC TCGGACTGGG       500

ACTGGAACCT CTCGGGGGGA CCATCATCGG GGAGTCACGT TACATCCTCA       550

GGTTCCCCAT TTTTGTATGT CCCCCCCTTC TGGGAGAGGC ACAGAGTCGA       600

CCTCGAGGTC CTATCACCGT GGACCTGTAC GTGACAGAAC GTCTTGGTCT       650

TCTTCCACCT CAAGTTTTAT CTGTAGCACC ACGATCGAAA GGTCTTCCGG       700
```

```
AGGTCGTATC AGATATTCTT TCTCCCCCTT GTCCACCTCA AGAGGAAGGG         750

TGAGCGGAAA TGTCAACTTT TCGACTGCCC GTCACCGCTC GACACCACCG         800

TCCGCCTCTC CCGAAGGAGG AGGTTCAGAA CCTAGTGGAA ACTGGACTTC         850

TTGTTCCTTC ACAGACATTT TGCCCAATGG GTCCTGGGAT TCGAGGTCTA         900

CCCGTTCTTC GAGGGCGAGG TGGAGTGGGA CGGGGTCCGG AACGGAGTCA         950

TACGACCGAG ACCTTTGGAG TGGGACCGGG AACTTCGCTT TTGTCCTTTC        1000

AACGTAGTCC TTCACTTGGA CCACCACTAC TCTCGGTGAG TCGAGGTCTT        1050

TTTAAACTGG ACACTCCACA CCCCTGGGTG GAGGGGATTC GACTACGACT        1100

CAAACTTTGA CCTCTTGTTC CTCCGTTTCC AGAGCTTCGC CCTCTTCCGC        1150

CACACCCACG ACTTGGGACT CCGCCCCTAC ACCGTCACAG ACGACTCACT        1200

GAGCCCTGTC CAGGACGACC TTAGGTTGTA GTTCCAAGAC GGGTGTACCA        1250

GGTGGGGCTC GAAATTACGC CATCAAATAG TGTCAATTTA ACGATTGCGT        1300

CAGTCCGTGG CACATACTTT AGATTGTTAC GCGAGTAGCA GTAGGAGCCG        1350

TGGCAGTGGG ACCTACGACA TCCGTATCCG AACCAATACG GCCATGACGG        1400

CCCGGAGAAC GCCCTA                                             1416
```

(2) INFORMATION FOR SEQ ID NO: 4:

(i) SEQUENCE CHARACTERISTICS:
        (A) LENGTH: 434 amino acids
        (B) TYPE: amino acid
        (D) TOPOLOGY: linear (xi) SEQUENCE DESCRIPTION: SEQ ID NO: 4:

```
Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Gln Gly Asn Lys Val
                50                  55                  60

Val Leu Gly Lys Lys Gly Asp Thr Val Glu Leu Thr Cys Thr Ala
                65                  70                  75

Ser Gln Lys Lys Ser Ile Gln Phe His Trp Lys Asn Ser Asn Gln
                80                  85                  90

Ile Lys Ile Leu Gly Asn Gln Gly Ser Phe Leu Thr Lys Gly Pro
                95                 100                 105

Ser Lys Leu Asn Asp Arg Ala Asp Ser Arg Arg Ser Leu Trp Asp
               110                 115                 120

Gln Gly Asn Phe Pro Leu Ile Ile Lys Asn Leu Lys Ile Glu Asp
               125                 130                 135

Ser Asp Thr Tyr Ile Cys Glu Val Glu Asp Gln Lys Glu Glu Val
               140                 145                 150

Gln Leu Leu Val Phe Gly Leu Thr Ala Asn Ser Asp Thr His Leu
               155                 160                 165

Leu Gln Gly Gln Ser Leu Thr Leu Thr Leu Glu Ser Pro Pro Gly
               170                 175                 180

Ser Ser Pro Ser Val Gln Cys Arg Ser Pro Arg Gly Lys Asn Ile
               185                 190                 195
```

Gln Gly Gly Lys Thr Leu Ser Val Ser Gln Leu Glu Leu Gln Asp
                200                 205                 210

Ser Gly Thr Trp Thr Cys Thr Val Leu Gln Asn Gln Lys Lys Val
                215                 220                 225

Glu Phe Lys Ile Asp Ile Val Val Leu Ala Phe Gln Lys Ala Ser
                230                 235                 240

Ser Ile Val Tyr Lys Lys Glu Gly Glu Gln Val Glu Phe Ser Phe
                245                 250                 255

Pro Leu Ala Phe Thr Val Glu Lys Leu Thr Gly Ser Gly Glu Leu
                260                 265                 270

Trp Trp Gln Ala Glu Arg Ala Ser Ser Lys Ser Trp Ile Thr
                275                 280                 285

Phe Asp Leu Lys Asn Lys Glu Val Ser Val Lys Arg Val Thr Gln
                290                 295                 300

Asp Pro Lys Leu Gln Met Gly Lys Lys Leu Pro Leu His Leu Thr
                305                 310                 315

Leu Pro Gln Ala Leu Pro Gln Tyr Ala Gly Ser Gly Asn Leu Thr
                320                 325                 330

Leu Ala Leu Glu Ala Lys Thr Gly Lys Leu His Gln Glu Val Asn
                335                 340                 345

Leu Val Val Met Arg Ala Thr Gln Leu Gln Lys Asn Leu Thr Cys
                350                 355                 360

Glu Val Trp Gly Pro Thr Ser Pro Lys Leu Met Leu Ser Leu Lys
                365                 370                 375

Leu Glu Asn Lys Glu Ala Lys Val Ser Lys Arg Glu Lys Ala Val
                380                 385                 390

Trp Val Leu Asn Pro Glu Ala Gly Met Trp Gln Cys Leu Leu Ser
                395                 400                 405

Asp Ser Gly Gln Val Leu Leu Glu Ser Asn Ile Lys Val Leu Pro
                410                 415                 420

Thr Trp Ser Thr Pro Ser Phe Asn Ala Val Val Tyr His Ser
                425                 430                 434

(2) INFORMATION FOR SEQ ID NO: 5:

(i) SEQUENCE CHARACTERISTICS:
       (A) LENGTH: 1508 bases
       (B) TYPE: nucleic acid
       (C) STRANDEDNESS: single
       (D) TOPOLOGY: linear (xi) SEQUENCE DESCRIPTION: SEQ ID NO: 5:

```
AAGCTTCAGC GCGAACGACC AACTACCCCG ATCATCAGTT ATCCTTAAGG           50

TCTCTTTTGT GTGGTGCGTT CCGGTATGGG GGGACTGCC GCCAGGTTGG           100

GGGCCGTGAT TTTGTTTGTC GTCATAGTGG GCCTCCATGG GGTCCGCGGC          150

AAATATGCCT TGGCGGATGC CTCTCTCAAG ATGGCCGACC CCAATCGATT          200

TCGCGGCAAA GACCTTCCGG TCCTGGACCA GCTGCTCGAG CAGGGAAACA          250

AAGTGGTGCT GGGCAAAAAA GGGGATACAG TGGAACTGAC CTGTACAGCT          300

TCCCAGAAGA AGAGCATACA ATTCCACTGG AAAAACTCCA ACCAGATAAA          350

GATTCTGGGA AATCAGGGCT CCTTCTTAAC TAAAGGTCCA TCCAAGCTGA          400

ATGATCGCGC TGACTCAAGA AGAAGCCTTT GGGACCAAGG AAACTTTCCC          450

CTGATCATCA AGAATCTTAA GATAGAAGAC TCAGATACTT ACATCTGTGA          500
```

```
AGTGGAGGAC CAGAAGGAGG AGGTGCAATT GCTAGTGTTC GGATTGACTG        550

CCAACTCTGA CACCCACCTG CTTCAGGGGC AGAGCCTGAC CCTGACCTTG        600

GAGAGCCCCC CTGGTAGTAG CCCCTCAGTG CAATGTAGGA GTCCAAGGGG        650

TAAAAACATA CAGGGGGGA AGACCCTCTC CGTGTCTCAG CTGGAGCTCC         700

AGGATAGTGG CACCTGGACA TGCACTGTCT TGCAGAACCA GAAGAAGGTG        750

GAGTTCAAAA TAGACATCGT GGTGCTAGCT TTCCAGAAGG CCTCCAGCAT        800

AGTCTATAAG AAAGAGGGGG AACAGGTGGA GTTCTCCTTC CCACTCGCCT        850

TTACAGTTGA AAAGCTGACG GGCAGTGGCG AGCTGTGGTG GCAGGCGGAG        900

AGGGCTTCCT CCTCCAAGTC TTGGATCACC TTTGACCTGA AGAACAAGGA        950

AGTGTCTGTA AAACGGGTTA CCCAGGACCC TAAGCTCCAG ATGGGCAAGA       1000

AGCTCCCGCT CCACCTCACC CTGCCCCAGG CCTTGCCTCA GTATGCTGGC       1050

TCTGGAAACC TCACCCTGGC CCTTGAAGCG AAAACAGGAA AGTTGCATCA       1100

GGAAGTGAAC CTGGTGGTGA TGAGAGCCAC TCAGCTCCAG AAAAATTTGA       1150

CCTGTCAGGT GTGGGACCC ACCTCCCCTA AGCTGATGCT GAGTTTGAAA        1200

CTGGAGAACA AGGAGGCAAA GGTCTCGAAG CGGGAGAAGG CGGTGTGGGT       1250

GCTGAACCCT GAGGCGGGGA TGTGGCAGTG TCTGCTGAGT GACTCGGGAC       1300

AGGTCCTGCT GGAATCCAAC ATCAAGGTTC TGCCCACATG GTCCACCCCG       1350

AGCTTTAATG CGGTAGTTTA TCACAGTTAA ATTGCTAACG CAGTCAGGCA       1400

CCGTGTATGA AATCTAACAA TGCGCTCATC GTCATCCTCG GCACCGTCAC       1450

CCTGGATGCT GTAGGCATAG GCTTGGTTAT GCCGGTACTG CCGGGCCTCT       1500

TGCGGGAT                                                     1508

(2) INFORMATION FOR SEQ ID NO: 6:

(i) SEQUENCE CHARACTERISTICS:
        (A) LENGTH: 1508 bases
        (B) TYPE: nucleic acid
        (C) STRANDEDNESS: single
        (D) TOPOLOGY: linear (xi) SEQUENCE DESCRIPTION: SEQ ID NO: 6:

TTCGAAGTCG CGCTTGCTGG TTGATGGGGC TAGTAGTCAA TAGGAATTCC         50

AGAGAAAACA CACCACGCAA GGCCATACCC CCCCTGACGG CGGTCCAACC        100

CCCGGCACTA AAACAAACAG CAGTATCACC CGGAGGTACC CCAGGCGCCG       150

TTTATACGGA ACCGCCTACG GAGAGAGTTC TACCGGCTGG GGTTAGCTAA        200

AGCGCCGTTT CTGGAAGGCC AGGACCTGGT CGACGAGCTC GTCCCTTTGT        250

TTCACCACGA CCCGTTTTTT CCCCTATGTC ACCTTGACTG GACATGTCGA        300

AGGGTCTTCT TCTCGTATGT TAAGGTGACC TTTTTGAGGT TGGTCTATTT        350

CTAAGACCCT TTAGTCCCGA GGAAGAATTG ATTTCCAGGT AGGTTCGACT        400

TACTAGCGCG ACTGAGTTCT TCTTCGGAAA CCCTGGTTCC TTTGAAAGGG        450

GACTAGTAGT TCTTAGAATT CTATCTTCTG AGTCTATGAA TGTAGACACT        500

TCACCTCCTG GTCTTCCTCC TCCACGTTAA CGATCACAAG CCTAACTGAC        550

GGTTGAGACT GTGGGTGGAC GAAGTCCCCG TCTCGGACTG GGACTGGAAC        600

CTCTCGGGGG GACCATCATC GGGGAGTCAC GTTACATCCT CAGGTTCCCC        650
```

-continued

```
ATTTTTGTAT GTCCCCCCCT TCTGGGAGAG GCACAGAGTC GACCTCGAGG          700
TCCTATCACC GTGGACCTGT ACGTGACAGA ACGTCTTGGT CTTCTTCCAC          750
CTCAAGTTTT ATCTGTAGCA CCACGATCGA AAGGTCTTCC GGAGGTCGTA          800
TCAGATATTC TTTCTCCCCC TTGTCCACCT CAAGAGGAAG GGTGAGCGGA          850
AATGTCAACT TTTCGACTGC CCGTCACCGC TCGACACCAC CGTCCGCCTC          900
TCCCGAAGGA GGAGGTTCAG AACCTAGTGG AAACTGGACT TCTTGTTCCT          950
TCACAGACAT TTTGCCCAAT GGGTCCTGGG ATTCGAGGTC TACCCGTTCT         1000
TCGAGGGCGA GGTGGAGTGG GACGGGGTCC GGAACGGAGT CATACGACCG         1050
AGACCTTTGG AGTGGGACCG GGAACTTCGC TTTTGTCCTT TCAACGTAGT         1100
CCTTCACTTG GACCACCACT ACTCTCGGTG AGTCGAGGTC TTTTTAAACT         1150
GGACACTCCA CACCCCTGGG TGGAGGGGAT TCGACTACGA CTCAAACTTT         1200
GACCTCTTGT TCCTCCGTTT CCAGAGCTTC GCCCTCTTCC GCCACACCCA         1250
CGACTTGGGA CTCCGCCCCT ACACCGTCAC AGACGACTCA CTGAGCCCTG         1300
TCCAGGACGA CCTTAGGTTG TAGTTCCAAG ACGGGTGTAC CAGGTGGGGC         1350
TCGAAATTAC GCCATCAAAT AGTGTCAATT TAACGATTGC GTCAGTCCGT         1400
GGCACATACT TTAGATTGTT ACGCGAGTAG CAGTAGGAGC CGTGGCAGTG         1450
GGACCTACGA CATCCGTATC CGAACCAATA CGGCCATGAC GGCCCGGAGA         1500
ACGCCCTA                                                      1508
```

(2) INFORMATION FOR SEQ ID NO: 7:

(i) SEQUENCE CHARACTERISTICS:
        (A) LENGTH: 371 amino acids
        (B) TYPE: amino acid
        (D) TOPOLOGY: linear (xi) SEQUENCE DESCRIPTION: SEQ ID NO: 7:

```
Val Thr Ala Ala Asp Thr Ala Val Tyr Tyr Cys Ala Arg Ala Thr
 1               5                  10                  15

Phe Cys Leu Trp Tyr Arg Glu Arg Pro Pro Cys Trp Ile Asp Pro
            20                  25                  30

Trp Gly Leu Gly Thr Leu Val Thr Val Ser Ser Ala Ser Thr Lys
            35                  40                  45

Gly Pro Ser Val Phe Pro Leu Ala Pro Ser Ser Lys Ser Thr Ser
            50                  55                  60

Gly Gly Thr Ala Ala Leu Gly Cys Leu Val Lys Asp Tyr Phe Pro
            65                  70                  75

Glu Pro Val Thr Val Ser Trp Asn Ser Gly Ala Leu Thr Ser Gly
            80                  85                  90

Val His Thr Phe Pro Ala Val Leu Gln Ser Ser Gly Leu Tyr Ser
            95                 100                 105

Leu Ser Ser Val Val Thr Val Pro Ser Ser Ser Leu Gly Thr Gln
           110                 115                 120

Thr Tyr Ile Cys Asn Val Asn His Lys Pro Ser Asn Thr Lys Val
           125                 130                 135

Asp Lys Lys Val Glu Pro Lys Ser Cys Asp Lys Thr His Thr Cys
           140                 145                 150

Pro Pro Cys Pro Ala Pro Glu Leu Leu Gly Gly Pro Ser Val Phe
           155                 160                 165
```

Leu Phe Pro Pro Lys Pro Lys Asp Thr Leu Met Ile Ser Arg Thr
                170                 175                 180

Pro Glu Val Thr Cys Val Val Val Asp Val Ser His Glu Asp Pro
            185                 190                 195

Glu Val Lys Phe Asn Trp Tyr Val Asp Gly Val Glu Val His Asn
            200                 205                 210

Ala Lys Thr Lys Pro Arg Glu Glu Gln Tyr Asn Ser Thr Tyr Arg
            215                 220                 225

Val Val Ser Val Leu Thr Val Leu His Gln Asp Trp Leu Asn Gly
            230                 235                 240

Lys Glu Tyr Lys Cys Lys Val Ser Asn Lys Ala Leu Pro Ala Pro
            245                 250                 255

Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn
            275                 280                 285

Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr
            305                 310                 315

Lys Thr Thr Pro Pro Val Leu Asp Ser Asp Gly Ser Phe Phe Leu
            320                 325                 330

Tyr Ser Lys Leu Thr Val Asp Lys Ser Arg Trp Gln Gln Gly Asn
            335                 340                 345

Val Phe Ser Cys Ser Val Met His Glu Ala Leu His Asn His Tyr
            350                 355                 360

Thr Gln Lys Ser Leu Ser Leu Ser Pro Gly Lys
            365                 370 371

(2) INFORMATION FOR SEQ ID NO: 8:

(i) SEQUENCE CHARACTERISTICS:
        (A) LENGTH: 1135 bases
        (B) TYPE: nucleic acid
        (C) STRANDEDNESS: single
        (D) TOPOLOGY: linear (xi) SEQUENCE DESCRIPTION: SEQ ID NO: 8:

GAATTCTGTC ACTGCCGCGG ACACGGCCGT ATATTACTGT GCGAGAGCCA        50

CCTTTTGCCT ATGGTACAGG GAGCGTCCCC CTTGTTGGAT CGACCCCTGG        100

GGCCTGGGAA CCCTGGTCAC CGTCTCCTCG GCCTCCACCA AGGGCCCATC        150

GGTCTTCCCC CTGGCACCCT CCTCCAAGAG CACCTCTGGG GGCACAGCGG        200

CCCTGGGCTG CCTGGTCAAG GACTACTTCC CCGAACCGGT GACGGTGTCG        250

TGGAACTCAG GCGCCCTGAC CAGCGGCGTG CACACCTTCC CGGCTGTCCT        300

ACAGTCCTCA GGACTCTACT CCCTCAGCAG CGTGGTGACC GTGCCCTCCA        350

GCAGCTTGGG CACCCAGACC TACATCTGCA ACGTGAATCA CAAGCCCAGC        400

AACACCAAGG TGGACAAGAA AGTTGAGCCC AAATCTTGTG ACAAAACTCA        450

CACATGCCCA CCGTGCCCAG CACCTGAACT CCTGGGGGGA CCGTCAGTCT        500

TCCTCTTCCC CCCAAAACCC AAGGACACCC TCATGATCTC CCGGACCCCT        550

GAGGTCACAT GCGTGGTGGT GGACGTGAGC CACGAAGACC CTGAGGTCAA        600

GTTCAAGTGG TACGTGGACG GCGTGGAGGT GCATAATGCC AAGACAAAGC        650

```
CGCGGGAGGA GCAGTACAAC AGCACGTACC GGGTGGTCAG CGTCCTCACC        700

GTCCTGCACC AGGACTGGCT GAATGGCAAG GAGTACAAGT GCAAGGTCTC        750

CAACAAAGCC CTCCCAGCCC CCATCGAGAA AACCATCTCC AAAGCCAAAG        800

GGCAGCCCCG AGAACCACAG GTGTACACCC TGCCCCCATC CCGGGATGAG        850

CTGACCAAGA ACCAGGTCAG CCTGACCTGC CTGGTCAAAG GCTTCTATCC        900

CAGCGACATC GCCGTGGAGT GGGAGAGCAA TGGGCAGCCG GAGAACAACT        950

ACAAGACCAC GCCTCCCGTG CTGGACTCCG ACGGCTCCTT CTTCCTCTAC       1000

AGCAAGCTCA CCGTGGACAA GAGCAGGTGG CAGCAGGGGA ACGTCTTCTC       1050

ATGCTCCGTG ATGCATGAGG CTCTGCACAA CCACTACACG CAGAAGAGCC       1100

TCTCCCTGTC TCCGGGTAAA TGAGTGCGAC GGCCG                       1135
```

(2) INFORMATION FOR SEQ ID NO: 9:

(i) SEQUENCE CHARACTERISTICS:
        (A) LENGTH: 1142 bases
        (B) TYPE: nucleic acid
        (C) STRANDEDNESS: single
        (D) TOPOLOGY: linear (xi) SEQUENCE DESCRIPTION: SEQ ID NO: 9:

```
CTTAAGACAG TGACGGCGCC TGTGCCGGCA TATAATGACA CGCTCTCGGT         50

GGAAAACGGA TACCATGTCC CTCGCAGGGG GAACAACCTA GCTGGGGACC        100

CCGGACCCTT GGGACCAGTG GCAGAGGAGC CGGAGGTGGT TCCCGGGTAG        150

CCAGAAGGGG GACCGTGGGA GGAGGTTCTC GTGGAGACCC CCGTGTCGCC        200

GGGACCCGAC GGACCAGTTC CTGATGAAGG GGCTTGGCCA CTGCCACAGC        250

ACCTTGAGTC CGCGGGACTG GTCGCCGCAC GTGTGGAAGG GCCGACAGGA        300

TGTCAGGAGT CCTGAGATGA GGGAGTCGTC GCACCACTGG CACGGGAGGT        350

CGTCGAACCC GTGGGTCTGG ATGTAGACGT TGCACTTAGT GTTCGGGTCG        400

TTGTGGTTCC ACCTGTTCTT TCAACTCGGG TTTAGAACAC TGTTTTGAGT        450

GTGTACGGGT GGCACGGGTC GTGGACTTGA GGACCCCCCT GGCAGTCAGA        500

AGGAGAAGGG GGGTTTTGGG TTCCTGTGGG AGTACTAGAG GGCCTGGGGA        550

CTCCAGTGTA CGCACCACCA CCTGCACTCG GTGCTTCTGG GACTCCAGTT        600

CAAGTTGACC ATGCACCTGC CGCACCTCCA CGTATTACGG TTCTGTTTCG        650

GCGCCCTCCT CGTCATGTTG TCGTGCATGG CCCACCAGTC GCAGGAGTGG        700

CAGGACGTGG TCCTGACCGA CTTACCGTTC CTCATGTTCA CGTTCCAGAG        750

GTTGTTTCGG GAGGGTCGGG GGTAGCTCTT TTGGTAGAGG TTTCGGTTTC        800

CCGTCGGGGC TCTTGGTGTC CACATGTGGG ACGGGGTAG GGCCCTACTC        850

GACTGGTTCT TGGTCCAGTC GGACTGGACG GACCAGTTTC CGAAGATAGG        900

GTCGCTGTAG CGGCACCTCA CCCTCTCGTT ACCCGTCGGC CTCTTGTTGA        950

TGTTCTGGTG CGGAGGGCAC GACCTGAGGC TGCCGAGGAA GAAGGAGATG       1000

TCGTTCGAGT GGCACCTGTT CTCGTCCACC GTCGTCCCCT TGCAGAAGAG       1050

TACGAGGCAC TACGTACTAC GTACTCCGAG ACGTGTTGGT GATGTGCGTC       1100

TTCTCGGAGA GGGACAGAGG CCCATTTACT CACGCTGCCG GC              1142
```

(2) INFORMATION FOR SEQ ID NO: 10:

(i) SEQUENCE CHARACTERISTICS:
        (A) LENGTH: 143 amino acids
        (B) TYPE: amino acid
        (D) TOPOLOGY: linear (xi) SEQUENCE DESCRIPTION: SEQ ID NO: 10:

```
Thr Leu Thr Ile Ser Gly Leu Gln Pro Glu Asp Phe Ala Thr Tyr
 1               5                  10                  15

Tyr Cys Gln Gln Tyr Lys Ser Leu Ser Leu Thr Phe Gly Gly Gly
                20                  25                  30

Thr Lys Val Glu Ile Lys Arg Thr Val Ala Ala Pro Ser Val Phe
                35                  40                  45

Ile Phe Pro Pro Ser Asp Glu Gln Leu Lys Ser Gly Thr Ala Ser
                50                  55                  60

Val Val Cys Leu Leu Asn Asn Phe Tyr Pro Arg Glu Ala Leu Val
                65                  70                  75

Gln Trp Leu Val Asp Asn Ala Leu Gln Ser Gly Asn Ser Gln Glu
                80                  85                  90

Ser Val Thr Glu Gln Asp Ser Lys Asp Ser Thr Tyr Ser Leu Ser
                95                 100                 105

Ser Thr Leu Thr Leu Ser Lys Ala Asp Tyr Glu Lys His Lys Val
               110                 115                 120

Tyr Ala Cys Glu Val Thr His Gln Gly Leu Ser Ser Pro Val Thr
               125                 130                 135

Lys Ser Phe Asn Arg Gly Glu Cys
               140         143
```

(2) INFORMATION FOR SEQ ID NO: 11:

(i) SEQUENCE CHARACTERISTICS:
        (A) LENGTH: 468 bases
        (B) TYPE: nucleic acid
        (C) STRANDEDNESS: single
        (D) TOPOLOGY: linear (xi) SEQUENCE DESCRIPTION: SEQ ID NO: 11:

```
GAATTCACTC TCACCATCAG CGGCCTGCAG CCTGAAGATT TTGCAACTTA          50
TTACTGCCAA CAGTATAAGA GTTTGTCGCT CACTTTCGGC GGAGGGACCA         100
AGGTGGAGAT CAAACGAACT GTGGCTGCAC CATCTGTCTT CATCTTCCCG         150
CCATCTGATG AGCAGTTGAA ATCTGGAACT GCCTCTGTTG TGTGCCTGCT         200
GAATAACTTC TATCCCAGAG AGGCCAAAGT ACAGTGGAAG GTGGATAACG         250
CCCTCCAATC GGGTAACTCC CAGGAGAGTG TCACAGAGCA GGACAGCAAG         300
GACAGCACCT ACAGCCTCAG CAGCACCCTG ACGCTGAGCA AAGCAGACTA         350
CGAGAAACAC AAAGTCTACG CCTGCGAAGT CACCCATCAG GGCCTGAGCT         400
CGCCCGTCAC AAAGAGCTTC AACAGGGGAG AGTGTTAGAG GGAGAAGTGC         450
CCCCACCTGC TCCTCAGT                                            468
```

(2) INFORMATION FOR SEQ ID NO: 12:

(i) SEQUENCE CHARACTERISTICS:
        (A) LENGTH: 468 bases
        (B) TYPE: nucleic acid
        (C) STRANDEDNESS: single
        (D) TOPOLOGY: linear (xi) SEQUENCE DESCRIPTION: SEQ ID NO: 12:

| | |
|---|---|
| CTTAAGTGAG AGTGGTAGTC GCCGGACGTC GGACTTCTAA AACGTTGAAT | 50 |
| AATGACGGTT GTCATATTCT CAAACAGCGA GTGAAAGCCG CCTCCCTGGT | 100 |
| TCCACCTCTA GTTTGCTTGA CACCGACGTG GTAGACAGAA GTAGAAGGGC | 150 |
| GGTAGACTAC TCGTCAACTT TAGACCTTGA CGGAGACAAC ACACGGACGA | 200 |
| CTTATTGAAG ATAGGGTCTC TCCGGTTTCA TGTCACCTTC CACCTATTGC | 250 |
| GGGAGGTTAG CCCATTGAGG GTCCTCTCAC AGTGTCTCGT CCTGTCGTTC | 300 |
| CTGTCGTGGA TGTCGGAGTC GTCGTGGGAC TGCGACTCGT TTCGTCTGAT | 350 |
| GCTCTTTGTG TTTCAGATGC GGACGCTTCA GTGGGTAGTC CCGGACTCGA | 400 |
| GCGGGCAGTG TTTCTCGAAG TTGTCCCCTC TCACAATCTC CCTCTTCACG | 450 |
| GGGGTGGACG AGGAGTCA | 468 |

(2) INFORMATION FOR SEQ ID NO: 13:

(i) SEQUENCE CHARACTERISTICS:
        (A) LENGTH: 44 bases
        (B) TYPE: nucleic acid
        (C) STRANDEDNESS: single
        (D) TOPOLOGY: linear (xi) SEQUENCE DESCRIPTION: SEQ ID NO: 13:

| | |
|---|---|
| AATTCAAGCC CAGAGCCCTG CCATTTCTGT GGGCTCAGGT CCCT | 44 |

(2) INFORMATION FOR SEQ ID NO: 14:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO: 14:

| | |
|---|---|
| ACTGCTCAGC CCCTTCCTCC CTCGGCAAGG CCACAATGAA CCGGGGAGTC | 50 |

(2) INFORMATION FOR SEQ ID NO: 15:

(i) SEQUENCE CHARACTERISTICS:
        (A) LENGTH: 47 bases
        (B) TYPE: nucleic acid
        (C) STRANDEDNESS: single
        (D) TOPOLOGY: linear (xi) SEQUENCE DESCRIPTION: SEQ ID NO: 15:

| | |
|---|---|
| CCTTTTAGGC ACTTGCTTCT GGTGCTGCAA CTGGCGCTCC TCCCAGC | 47 |

(2) INFORMATION FOR SEQ ID NO: 16:

(i) SEQUENCE CHARACTERISTICS:
        (A) LENGTH: 61 bases
        (B) TYPE: nucleic acid
        (C) STRANDEDNESS: single
        (D) TOPOLOGY: linear (xi) SEQUENCE DESCRIPTION: SEQ ID NO: 16:

| | |
|---|---|
| AGCCACTCAG GGAAACAAAG TGGTGCTGGG CAAAAAAGGG GATACAGTGG | 50 |
| AACTGACCTG T | 61 |

(2) INFORMATION FOR SEQ ID NO: 17:

```
    (i) SEQUENCE CHARACTERISTICS:
        (A) LENGTH: 51 bases
        (B) TYPE: nucleic acid
        (C) STRANDEDNESS: single
        (D) TOPOLOGY: linear (xi) SEQUENCE DESCRIPTION: SEQ ID NO: 17:

ACAGGTCAGT TCCACTGTAT CCCCTTTTTT GCCCAGCACC ACTTTGTTTC           50

C                                                                51

(2) INFORMATION FOR SEQ ID NO: 18:

(i) SEQUENCE CHARACTERISTICS:
        (A) LENGTH: 47 bases
        (B) TYPE: nucleic acid
        (C) STRANDEDNESS: single
        (D) TOPOLOGY: linear (xi) SEQUENCE DESCRIPTION: SEQ ID NO: 18:

CTGAGTGGCT GCTGGGAGGA GCGCCAGTTG CAGCACCAGA AGCAAGT              47

(2) INFORMATION FOR SEQ ID NO: 19:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO: 19:

GCCTAAAAGG GACTCCCCGG TTCATTGTGG CCTTGCCGAG GGAGGAAGGG           50

(2) INFORMATION FOR SEQ ID NO: 20:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO: 20:

GCTGAGCAGT AGGGACCTGA GCCCACAGAA ATGGCAGGGC TCTGGGCTTG           50

(2) INFORMATION FOR SEQ ID NO: 21:

(i) SEQUENCE CHARACTERISTICS:
        (A) LENGTH: 59 bases
        (B) TYPE: nucleic acid
        (C) STRANDEDNESS: single
        (D) TOPOLOGY: linear (xi) SEQUENCE DESCRIPTION: SEQ ID NO: 21:

CTGCTCGAGC AGGGAAACAA AGTGGTGCTG GGCAAAAAAG GGGATACAGT           50

GGAACTGAC                                                        59

(2) INFORMATION FOR SEQ ID NO: 22:

(i) SEQUENCE CHARACTERISTICS:
        (A) LENGTH: 59 bases
        (B) TYPE: nucleic acid
        (C) STRANDEDNESS: single
        (D) TOPOLOGY: linear (xi) SEQUENCE DESCRIPTION: SEQ ID NO: 22:

ACAGGTCAGT TCCACTGTAT CCCCTTTTTT GCCCAGCACC ACTTTGTTTC           50
```

-continued

```
CCTGCTCGA                                                         59

(2) INFORMATION FOR SEQ ID NO: 23:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO: 23:

CGTGATAGAA GCTTTCTAGA G                                           21

(2) INFORMATION FOR SEQ ID NO: 24:

(i) SEQUENCE CHARACTERISTICS:
        (A) LENGTH: 51 bases
        (B) TYPE: nucleic acid
        (C) STRANDEDNESS: single
        (D) TOPOLOGY: linear (xi) SEQUENCE DESCRIPTION: SEQ ID NO: 24:

CCCTTTTTTG CCCAGCACCA CCTTCTTGCC CTGAGTGGCT GCTGGGAGGA            50

G                                                                 51

(2) INFORMATION FOR SEQ ID NO: 25:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO: 25:

CCACCTTCTT GCCCTG                                                 16
```